US010564165B2

(12) United States Patent
Delamarre et al.

(10) Patent No.: US 10,564,165 B2
(45) Date of Patent: Feb. 18, 2020

(54) IDENTIFICATION OF IMMUNOGENIC MUTANT PEPTIDES USING GENOMIC, TRANSCRIPTOMIC AND PROTEOMIC INFORMATION

(71) Applicant: GENENTECH, INC., South San Francisco, CA (US)

(72) Inventors: Lelia Delamarre, San Francisco, CA (US); Patrick Lupardus, San Francisco, CA (US); Ira Mellman, San Francisco, CA (US); Mahesh Yadav, San Francisco, CA (US); Suchit Jhunjhunwala, Sunnyvale, CA (US); Jennie Lill, Pacifica, CA (US)

(73) Assignee: GENENTECH, INC., South San Francisco, CA (US)

( * ) Notice: Subject to any disclaimer, the term of this patent is extended or adjusted under 35 U.S.C. 154(b) by 915 days.

(21) Appl. No.: 14/850,864

(22) Filed: Sep. 10, 2015

(65) Prior Publication Data
US 2016/0069895 A1 Mar. 10, 2016

Related U.S. Application Data

(60) Provisional application No. 62/048,742, filed on Sep. 10, 2014.

(51) Int. Cl.
G01N 33/68 (2006.01)
C12Q 1/6886 (2018.01)
A61K 39/00 (2006.01)
G01N 33/569 (2006.01)

(52) U.S. Cl.
CPC ......... G01N 33/6848 (2013.01); A61K 39/00 (2013.01); A61K 39/0011 (2013.01); C12Q 1/6886 (2013.01); G01N 33/56977 (2013.01); G01N 33/6878 (2013.01); A61K 2039/55516 (2013.01); A61K 2039/55561 (2013.01); C12Q 2600/156 (2013.01); G01N 2333/70539 (2013.01); G01N 2800/7028 (2013.01)

(58) Field of Classification Search
None
See application file for complete search history.

(56) References Cited

U.S. PATENT DOCUMENTS

| | | | |
|---|---|---|---|
| 8,140,270 B2 | 3/2012 | Kingsmore | |
| 8,217,016 B2 | 7/2012 | Hoerr et al. | |
| 8,349,558 B2 | 1/2013 | Fatho et al. | |
| 9,791,443 B2 | 10/2017 | Weinschenk et al. | |
| 2005/0221350 A1 | 10/2005 | Weinschenk et al. | |
| 2008/0166340 A1 | 7/2008 | Türeci et al. | |
| 2009/0104186 A1 | 4/2009 | Eberts et al. | |
| 2010/0151492 A1 | 6/2010 | Ahmed et al. | |
| 2011/0014628 A1 | 1/2011 | Türeci et al. | |
| 2011/0257890 A1 | 10/2011 | Weinschenk et al. | |

FOREIGN PATENT DOCUMENTS

| | | |
|---|---|---|
| CN | 1211279 A | 3/1999 |
| CN | 103180730 A | 6/2013 |
| JP | 2012-510619 A | 5/2012 |
| JP | 2013-525759 A | 6/2013 |
| WO | WO-1994/023031 A1 | 10/1994 |
| WO | WO9725426 A2 | 7/1997 |
| WO | WO9725426 A3 | 10/1997 |
| WO | WO-1998/14464 A1 | 4/1998 |
| WO | WO-1999/24566 A1 | 5/1999 |
| WO | WO-2000/20029 A1 | 4/2000 |
| WO | WO-2001/47959 A2 | 7/2001 |
| WO | WO-2001/47959 A3 | 7/2001 |
| WO | WO-2011/143656 A2 | 11/2001 |
| WO | WO-2011/143656 A3 | 11/2001 |
| WO | WO-2003/051401 A2 | 12/2003 |
| WO | WO-2003/051401 A3 | 12/2003 |
| WO | WO-2003/106692 A2 | 12/2003 |
| WO | WO-2003/106692 A3 | 12/2003 |
| WO | WO-2005/030250 A2 | 4/2005 |
| WO | WO-2005/030250 A3 | 4/2005 |
| WO | WO-2005/110338 A2 | 11/2005 |
| WO | WO-2005/110338 A3 | 11/2005 |
| WO | WO-2007/025760 A2 | 3/2007 |
| WO | WO-2007/025760 A3 | 3/2007 |
| WO | WO-2007/031222 A2 | 3/2007 |
| WO | WO-2007/031222 A3 | 3/2007 |
| WO | WO-2007/101227 A2 | 9/2007 |

(Continued)

OTHER PUBLICATIONS

Yadav, Mahesh, et al. "Predicting immunogenic tumour mutations by combining mass spectrometry and exome sequencing." Nature 515.7528 (2014): 572.*
Pardoll, Drew M. "The blockade of immune checkpoints in cancer immunotherapy." Nature Reviews Cancer 12.4 (2012): 252.*
Bentley, D.R. et al.(Nov. 6, 2008). "Accurate Whole Human Genome Sequencing Using Reversible Terminator Chemistry," *Nature* 456(7218):53-59, 20 pages.
Brickner, A.G. et al. (Jan. 15, 2001). "The Immunogenicity of a New Human Minor Histocompatibility Antigen Results From Differential Antigen Processing," *J. Exp. Med.* 193(2):195-205.
Calis, J.J.A. et al. (Oct. 24, 2013). "Properties of MHC Class I Presented Peptides That Enhance Immunogenicity," *PLOS Computational Biology* 9(10)(e1003266):1-13.

(Continued)

Primary Examiner — G Steven Vanni
(74) Attorney, Agent, or Firm — Morrison & Foerster LLP

(57) ABSTRACT

The present disclosure provides methods of identifying a disease-specific immunogenic peptide through a series of selection steps. Immunogenic epitopes identified by methods of the present disclosure are applicable for use in peptide-based immunotherapy, preferably cancer therapy. Furthermore, the methods of the present disclosure may be performed in a high-throughput manner and serve as a means of personalized vaccine development and therapy. Also provided are compositions of immunogenic peptides as well as methods of treatment comprising said compositions.

11 Claims, 10 Drawing Sheets
Specification includes a Sequence Listing.

(56) References Cited

FOREIGN PATENT DOCUMENTS

| WO | WO-2007/101227 A3 | 9/2007 |
|---|---|---|
| WO | WO-2007/101227 A8 | 9/2007 |
| WO | WO-2008/080468 A1 | 7/2008 |
| WO | WO-2009/053041 A2 | 4/2009 |
| WO | WO-2009/053041 A3 | 4/2009 |
| WO | WO-2010/063011 A2 | 6/2010 |
| WO | WO-2010/063011 A3 | 6/2010 |
| WO | WO-2011/128448 A1 | 10/2011 |
| WO | WO-2012/159643 A1 | 11/2012 |
| WO | WO-2012/159754 A2 | 11/2012 |
| WO | WO-2012/159754 A3 | 11/2012 |
| WO | WO-2013/040142 A2 | 3/2013 |
| WO | WO-2013/040142 A3 | 3/2013 |
| WO | WO-2014/012051 A1 | 1/2014 |
| WO | WO-2014/082729 A1 | 6/2014 |
| WO | WO-2014/168874 A2 | 10/2014 |
| WO | WO-2014/168874 A3 | 10/2014 |
| WO | WO-2014/180490 A1 | 11/2014 |
| WO | WO-2014/180569 A1 | 11/2014 |
| WO | WO-2015/014375 A1 | 2/2015 |
| WO | WO-2015/058780 A1 | 4/2015 |
| WO | WO-2015/172843 A1 | 11/2015 |
| WO | WO-2016/062323 A1 | 4/2016 |

OTHER PUBLICATIONS

Castle, J.C. et al. (2012, e-pub. Jan. 11, 2012). "Exploiting the Mutanome for Tumor Vaccination," *Cancer Res.* 72:1081-1091.
Chen, W. et al. (Jun. 4, 2001). "Immunoproteasomes Shape Immunodominance Hierarchies of Antiviral CD8+T Cells at the Levels of T Cell Repertoire and Presentation of Viral Antigens," *The Journal of Experimental Medicine* 193(11):1319-1326.
Chivian, D. et al. (2006, e-pub. Sep. 13, 2006). "Homology Modeling Using Parametric Alignment Ensemble Generation With Consensus and Energy-Based Model Selection," *Nucleic Acids Research* 34(17):e112, 1-18 pages.
Choi, M. et al. (Nov. 10, 2009). Genetic Diagnosis by Whole Exome Capture and Massively Parallel DNA Sequencing, *Proceedings of the National Academy of Sciences* 106(45):19096-19101.
Coulie, P.G. et al. (Aug. 1995). "A Mutated Intron Sequence Codes for an Antigenic Peptide Recognized by Cytolytic T Lymphocytes on a Human Melanoma," *Proc. Natl. Acad. Sci. USA* 92:7976-7980.
Ding et al. (Apr. 15, 2010). "Genome Remodeling in a Basal-like Breast Cancer Metastasis and Xenograft," *Nature* 464(7291):999-1005.
German, M. A et al. (Aug. 2008). "Global Identification of MicroRNA-Target RNA Pairs by Parallel Analysis of RNA Ends," *Nature Biotechnology* 26(8):941-946.
Ghaemmaghami, S. et al. (Oct. 16, 2003). "Global Analysis of Protein Expression in Yeast," *Nature* 425:737-741.
Hacohen, N. et al. (Feb. 18, 2014). "Declaration of Nir Hacohen under 37 CFR 1.132," 10 pages.
Hannani, D. et al. (Sep./Oct. 2011). "Prerequisites for the Antitumor Vaccine-Like Effect of chemotherapy and Radiotherapy," *Cancer J.* 17(5):351-358.
La Gruta, N.L. et al. (Jan. 24, 2006). "A Virus-specific CD8+T Cell Immunodominance Hierarchy Determined by Antigen Dose and Precursor Frequencies," *Proceedings of the National Academy of Sciences* 103(4): 994-999.
Lennerz, V. et al. (Nov. 1, 2005). "The Response of Autologous T Cells to a Human Melanoma is Dominated by Mutated Neoantigens," *Proc. Natl. Acad. Sci. USA* 102(44):16013-16018.
Ley, T.J. et al. (Nov. 6, 2008). "DNA Sequencing of a Cytogenetically Normal Acute Myeloid Leukaemia Genome," *Nature* 456:66-72.
Lijin, L. et al. (Nov. 25, 2011). "Cancer Genome Sequencing and its Implications for Personalized Cancer Vaccines," *Cancers, Molecular Diversity Preservation International* 3(4):4191-4211.
Maksyutov, A.Z. et al. (1993). "ADEPT: A Computer Program for Prediction of Protein Antigenic Determinants," *Comput. Appl. Biosci.* 9(3):291-297.
Mandelboim, O. et al. (Nov. 1995). "Regression of Established Murine Carcinoma Metastases Following Vaccination With Tumour-Associated Antigen Peptides," *Nature Medicine* 1(11):1179-1183.
Marti-Renom, M.A. et al. (2000). "Comparative Protein Structure Modeling of Genes and Genomes," *Annual Review of Biophysics and Biomolecular Structure* 29:291-325.
McRobb, F.M. et al. (2010, e-pub. Mar. 1, 2010). "Homology Modeling and Docketing Evaluation of Aminergic G Protein-Coupled Receptors," *Journal of Chemical Information and Modeling* 50:626-637.
Monach, P.A. et al. (Jan. 1995). "A Unique Tumor Antigen Produced by a Single Amino Acid Substitution," *Immunity* 2:45-59.
Mortazavi, A. (Jul. 2008, e-pub. May 30, 2008). "Mapping and Quantifying Mammalian Transcriptomes by RNA-Seq," *Nature Methods* 5(7):621-628.
Moutaftsi, M. et al. (Jul. 2006. E-pub. Jun. 11, 2006). "A consensus epitope prediction approach identifies the breadth of murine $T_{CD8+}$-Cell Responses to Vaccina Virus," *Nature Biotechnology* 24(7):817-819.
Ng, S.B. et al. (Sep. 10, 2009). "Targeted Capture and Massively Parallel Sequencing of 12 Human Exomes," *Nature* 461:272-276.
Ozsolak, F. et al. (Feb. 2011, e-pub. Dec. 30, 2010). "RNA Sequencing: Advances, Challenges and Opportunities," *Nature Reviews* 12:87-98.
Park, M.-S. et al. (Nov. 2013). "Accurate Structure Prediction of Peptide-MHC Complexes for Identifying Highly Immunogenic Antigens," *Molecular Immunology* 56(0):81-90, 25 pages.
Rammensee, H. et al. (Nov. 1999). "SYFPEITHI: Database for MHC Ligands and Peptide Motifs," *Immunogenentics* 50(3-4):213-219.
Rammensee, H.G. et al. (Oct. 2002). "Towards Patient-Specific Tumor Antigen Selection for Vaccination," *Immunol. Rev.* 188:164-176.
Rammensee, H.G. (Jun. 2006). "Special Feature: Some Considerations on the Use of Peptides and mRNA for Therapeutic Vaccination Against Cancer," *Immunol. Cell Biol.* 84(3):290-294.
Sahin, U. et al. (1998). "Letter to the Editor: Expression of Multiple Cancer/Testis (CT) Antigens in Breast Cancer and Melanoma: Basis for Polyvalent CT Vaccine Strategies," *Int. J. Cancer* 78:387-389.
Segal et al. (Feb. 1, 2008). "Epitope Landscape in Breast and Colorectal Cancer," *Cancer Res.* 68(3):889-892.
Sensi, M. et al. (Sep. 1, 2006). "Unique Tumor Antigens: Evidence for Immune Control of Genome Integrity and Immunogenic Targets for T Cell-Mediated Patient-Specific Immunotherapy," *Clin. Cancer Res.* 12(17):5023-5032.
Shah, S.P. et al. (Jun. 25, 2009). "Mutation of FOXL2 in Granulosa-Cell Tumors of the Ovary," *N. Eng. J. Med.* 360(26):2719-2729.
Sjöblom, T. et al. (Oct. 13, 2006). "The Consensus Coding Sequences of Human Breast and Colorectal Cancers," *Science* 314:268-274.
Stephens, P. et al. (2005, e-pub. May 22, 2005). "A Screen of the Complete Protein Kinase Gene Family Identifies Diverse Patterns of Somatic Mutations in Human Breast Cancer," *Nature Genetics* 37:590-592.
Sturniolo, T. et al. (Jun. 1999). "Generation of Tissue-Specific and Promiscuous HLA Ligand Databases Using DNA Microarrays and Virtual HLA Class II Matrices," *Nature Biotechnol.* 17:555-561.
Tang, F. et al. (May 2009). "mRNA-Seq Whole-Transcriptome Analysis of a Single Cell," *Nature Methods* 6(5):377-382.
Tung, C.-W. et al. (2011). "POPISK: T-Cell Reactivity Prediction Using Support Vector Machines and String Kernels," *BMC Bioinformatics* 12(446):1-12.
Van Laere, A.S. et al. (Oct. 23, 2003). "A Regulatory Mutation in IGF2 Causes a Major QTL Effect on Muscle Growth in the Pig," *Nature* 425(6960):832-836.
Wang, Z. et al. (Jan. 2009). "RNA-Seq: A Revolutionary Tool for Transcriptomics," *Nature Reviews* 10:57-63.
Weinschenk et al. (Oct. 15, 2002). "Integrated Functional Genomics Approach for the Design of Patient-Individual Antitumor Vaccines," *Cancer Res* 62:5818-5827.
Wittman, V.P. et al. (2006). "Antibody Targeting to a Class I MHC-Peptide Epitope Promotes Tumor Cell Death," *J. of Immunol.* 177:4187-4195.

(56) References Cited

OTHER PUBLICATIONS

Wood et al. (Nov. 16, 2007). "The Genomic Landscapes of Human Breast and Colorectal Cancers," *Science* 318:1108-1113.
Wortzel et al. (Jul. 14, 1983). "Multiple Tumour-Specific Antigens Expressed on a Single Tumour Cell," *Nature* 304:165-167.
Wu, T.D. et al. (Feb. 10, 2010). "Fast and SNP-Tolerant Detection of Complex Variants and Splicing in Short Reads," *Bioinformatics* 26:873-881.
International Search Report dated Dec. 23, 2015, for PCT Patent Application No. PCT/US2015/049491, filed on Sep. 10, 2015, 6 pages.
Written Opinion dated Dec. 23, 2015, for PCT Patent Application No. PCT/US2015/049491, filed on Sep. 10, 2015, 8 pages.
Communication Pursuant to Article 94(3) EPC, for European Patent Application No. 15772084.8, dated Jul. 17, 2018, 4 pages.
Dudek, N.L. (Nov. 2012, e-pub. Aug. 7, 2012). "Constitutive and Inflammatory Immunopeptidome of Pancreatic β-Cells," *Diabetes* 61:3018-3025.

\* cited by examiner

IDENTIFICATION OF IMMUNOGENIC MUTANT PEPTIDES USING GENOMIC, TRANSCRIPTOMIC AND PROTEOMIC INFORMATION

CROSS REFERENCE TO RELATED APPLICATIONS

This application claims priority of U.S. Provisional Application No. 62/048,742, filed Sep. 10, 2014, all of which is incorporated herein by reference in its entirety for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392027600SeqList.txt, date recorded: Sep. 9, 2015, size: 6 KB).

FIELD OF THE DISCLOSURE

The present disclosure is directed to methods of identifying mutant peptides useful for developing immunotherapeutics.

BACKGROUND OF THE DISCLOSURE

Cytotoxic T-lymphocytes (cytotoxic T cells or CD8 T cells) involved in cell-mediated immunity monitor changes in cellular health by scanning peptide epitopes, or antigens, on cell surfaces. Peptide epitopes originate from cellular proteins and serve as a display mechanism that allows cells to present evidence of current cellular processes. Both native and non-native proteins (often referred to as self and non-self, respectively) are processed for peptide epitope presentation. Most self peptides are derived from natural protein turnover and defective ribosomal products. Non-self peptides may be derived from proteins produced in the course of events such as viral and bacterial infection, disease, and cancer.

Human tumors characteristically harbor a remarkable number of somatic mutations. In turn, expression of a peptide containing a mutation may be recognized as a non-self neoepitope by the adaptive immune system. Upon recognition of a non-self antigen, cytotoxic T cells will trigger an immune response resulting in apoptosis of cells displaying the non-self neoepitope. The cytotoxic T cell immune response is a highly specific mechanism of the adaptive immune system and is an efficient means for eliminating infected, diseased, and cancerous cells. There is a large therapeutic value in identifying immunogenic epitopes as exposure to immunogenic epitopes via vaccination may be used to trigger a desired cytotoxic T cell immune response. The role of immunogenic epitopes has been known in the scientific and medical community for decades, but the identification of antigens driving effective anti-tumor CD8 T cell responses remains largely unknown. The complexity involved with epitope presentation and cytotoxic T cell activation has mired their discovery and therapeutic use.

Major histocompatibility complex (MHC) class I molecules are responsible for peptide epitope presentation to cytotoxic T cells. In humans, the human leukocyte antigen (HLA) system is a locus of genes that code for MHC class I and class II molecules. HLA-A, -B, and -C genes code for MHC class I (MHCI) proteins. A peptide, typically 8-11 amino acids in length, will bind an MHCI molecule through interaction with a groove formed by two alpha helices positioned above an antiparallel beta sheet. Processing and presentation of peptide-MHC class I (pMHCI) molecules involve a series of sequential stages comprising: a) protease-mediated digestion of proteins; b) peptide transport into the endoplasmic reticulum (ER) mediated by the transporter associated with antigen processing (TAP); c) formation of pMHCI using newly synthesized MHCI molecules; and, d) transport of pMHCI to the cell surface.

On the cell surface, pMHCI will interact with cytotoxic T cells via T cell receptors (TCRs). Following the intricate pMHCI-TCR interaction, identification of a non-self antigen may result in cytotoxic T cell activation through a series of biochemical events mediated by associated enzymes, co-receptors, adaptor molecules, and transcription factors. An activated cytotoxic T cell will proliferate to produce a population of effector T cells expressing TCRs specific to the identified immunogenic peptide epitope. The amplification of T cells with TCR specificity to the identified non-self epitope results in immune-mediated apoptosis of cells displaying the activating non-self epitope.

The use of immunogenic epitopes to activate the immune system is currently being investigated for use in cancer therapy. While cancer cells originate from normal tissue, somatic mutations drive a large number of changes in the cancer proteasome. In turn, the resulting MHCI presented peptide epitopes, referred to as tumor-associated antigens (TAAs) or neoepitopes, allow for cytotoxic T cell differentiation between normal and cancer tissue. Recent work has confirmed that mutant peptides can serve as epitopes recognized as non-self by CD4 or CD8 T cells, but few mutant neoepitopes have been described since.

The use of peptide-based immunotherapy hinges on selection of a peptide epitope that will stimulate a desired cytotoxic T cell response. Specifically, tumor antigens can be classified into two categories: tumor-associated self-antigens (e.g., cancer-testis antigens, differentiation antigens) and antigens derived from shared or patient-specific mutant proteins. Since the presentation of self-antigens in the thymus may result in the elimination of high avidity T cells, mutant neoantigens are likely to be more immunogenic. The development of such immunotherapeutic epitopes is a challenging pursuit and efficient methods useful for the identification of efficacious epitopes are yet to be developed.

The time and cost intensive nature involved in the identification and verification of immunogenic peptide epitopes has hampered the development of efficacious peptide-based cancer vaccinations. To further complicate the issues involved in identifying immunogenic epitopes, permutations of mutations in cancer cells are often patient specific. The discovery of a mutant neoepitope requires laborious screening of a patient's tumor infiltrating lymphocytes for their ability to recognize an antigen from libraries constructed based on information from that patient's tumor exome sequence. Alternatively, mutant neoepitopes may be detected by mass spectrometry. However, mutant sequences have evaded detection because use of public proteomic databases that do not contain patient-specific mutations do not allow for their identification. The use of predictive algorithms, such as peptide-MHCI binding or peptide immunogenicity, may have potential application in the identification of personalized immunogenic epitopes. But, the vast number of somatic mutations and expression level changes contained in cancer cells results in a magnitude of predicted immunogenic epitopes too large for high-throughput immunogenic screening. Further, evidence of the poor immunogenicity of predicted epitopes calls into question the utility of current methodology.

There is need in the art to identify immunogenic epitopes suitable for use in peptide-based immunotherapy. Specifically, there is need in the art to identify immunogenic epitopes for use in peptide-based cancer therapy. Furthermore, there is need in the art for high-throughput methodology for prediction of immunogenic epitopes based on personalized genetic and/or proteomic analysis.

All references cited herein are hereby specifically incorporated by reference.

SUMMARY OF THE DISCLOSURE

The present application in one aspect provides a method of identifying a disease-specific immunogenic mutant peptide, comprising a) providing a set of variant-coding sequences of the disease tissue in the individual, each variant-coding sequence having a variation in the sequence compared to a reference sample, and b) selecting immunogenic variant-coding sequences from the set of variant-coding sequences, wherein the selecting step comprises predicting immunogenicity of the peptides comprising a variant amino acid encoded by the variant-coding sequences, thereby identifying the disease-specific immunogenic mutant peptide. In some embodiments, the method comprises a) obtaining a first set of variant-coding sequences based on the genomic sequence of the disease tissue in the individual, each variant-coding sequence having a variation in the sequence compared to a reference sample, b) selecting a second set of expression variant-coding sequences from the first set based on the transcriptomic sequence of the disease tissue in the individual, c) selecting a third set of epitope variant-coding sequences from the second set based on predicted ability of the peptides encoded by the expression variant-coding sequences to bind to an MHC class I molecule (MHCI), and d) selecting immunogenic variant-coding sequences from the third set comprising predicting immunogenicity of the peptides comprising a variant amino acid encoded by the epitope variant-coding sequences, thereby identifying the disease-specific immunogenic mutant peptide.

In some embodiments, according to any of the methods described above, the method further comprises i) obtaining a plurality of peptides that are bound to an MHCI molecule from the disease tissue, ii) subjecting the MHCI-bound peptides to mass spectrometry-based sequencing, and iii) correlating the mass spectrometry-derived sequence information of the MHCI-bound peptides with the immunogenic variant-coding sequences.

The present application in another aspect provides a method of identifying a disease-specific immunogenic mutant peptide, comprising a) obtaining a plurality of peptides that are bound to an MHC molecule from a diseased tissue of an individual, b) subjecting the MHC-bound peptides to mass spectrometry-based sequencing, and c) correlating the mass spectrometry-derived sequence information of the MHC-bound peptides with a set of variant-coding sequences of the disease tissue in the individual, each variant-coding sequence having a variation in the sequence compared to a reference sample, thereby identifying the disease-specific immunogenic mutant peptide.

In some embodiments, the method comprises a) obtaining a first set of variant-coding sequences based on the genomic sequences of the disease tissue in the individual, each variant-coding sequence having a variation in the sequence compared to a reference sample, b) selecting a second set of expression variant-coding sequences from the first set based on transcriptomic sequences of the disease tissue in the individual, c) selecting a third set of epitope variant-coding sequences from the second set based on predicted ability of the peptides encoded by the expression variant-coding sequences to bind to an MHC class I molecule (MHCI), d) obtaining a plurality of peptides that are bound to an MHCI molecule from the disease tissue, e) subjecting the MHCI-bound peptides to mass spectrometry-based sequencing, and f) correlating the mass spectrometry-derived sequence information of the MHCI-bound peptides with the third set of epitope variant-coding sequences, thereby identifying the disease-specific immunogenic mutant peptide. In some embodiments, the method further comprises predicting immunogenicity of the disease-specific immunogenic mutant peptides, wherein the disease-specific immunogenic mutant peptide comprises a variant amino acid.

According to any of the methods described above that comprises a step of predicting immunogenicity, predicting immunogenicity is based on one or more of the following parameters: i) binding affinity of the peptide to the MHCI molecule; ii) protein level of a peptide precursor containing the peptide; iii) expression level of the transcript encoding the peptide precursor; iv) processing efficiency of the peptide precursor by an immunoproteasome; v) timing of the expression of the transcript encoding the peptide precursor; vi) binding affinity of the peptide to a TCR molecule; vii) position of a variant amino acid within the peptide; viii) solvent exposure of the peptide when bound to a MHCI molecule; ix) solvent exposure of the variant amino acid when bound to a MHCI molecule; x) content of aromatic residues in the peptide; xi) properties of the variant amino acid when compared to the wild type residue; and xii) nature of the peptide precursor. In some embodiments, predicting immunogenicity is further based on HLA-typing analysis.

In some embodiments, according to any one of the methods described above that comprises a step of obtaining a plurality of peptides that are bound to an MHCI molecule from disease tissue, the peptides bound to MHCI are obtained by isolating MHCI/peptide complexes from the disease tissue and eluting the peptides from the MHCI. In some embodiments, the isolation of MHCI/peptide complexes is carried out by immunoprecipitation. In some embodiments, the immunoprecipitation is carried out using an antibody specific for MHCI. In some embodiments, the isolated peptides are further separated by chromatography prior to being subjected to mass spectrometry.

In some embodiments, according to any one on the methods described above that comprises the step of obtaining a first set of variant-coding sequences, obtaining a first set of variant-coding sequences comprises i) obtaining a first set of variant sequences based on the genomic sequences of the disease tissue in the individual, each variant sequence having a variation in the sequence compared to a reference sample, and ii) identifying the variants coding-sequences from the first set of variant sequences.

In some embodiments, according to any of the methods described above, wherein the method further comprises synthesizing a peptide based on the sequence of the identified disease-specific immunogenic mutant peptide. In some embodiments, according to any of the methods described above, the method further comprises synthesizing a nucleic acid encoding a peptide based on the sequence of the identified disease-specific immunogenic mutant peptide. In some embodiments, the method further comprises testing the synthesized peptide for immunogenicity in vivo.

In some embodiments, according to any of the methods described above, the disease is cancer. In some embodiments, according to any of the methods described above, the individual is human.

The present application in another aspect also provides a disease-specific mutant peptide or compositions of a disease-specific mutant peptide identified by any of the methods described herein. In some embodiments, the composition comprises two or more disease-specific immunogenic mutant peptides described herein. In some embodiments, the composition further comprises an adjuvant.

The present application in yet another aspect also provides a method of treating a disease in an individual, comprising administering to the individual an effective amount of a composition comprising a disease-specific mutant peptide identified with any of the methods for identifying a disease-specific immunogenic mutant peptide disclose herein. In some embodiments, the individual is the same individual from whom the disease-specific immunogenic mutant peptide is identified.

The present application also provides an immunogenic composition comprising at least one disease-specific peptide or a precursor of such disease-specific peptide, wherein said disease-specific peptide is identified by any of the methods described herein. In some embodiments, the immunogenic composition comprises a plurality of disease-specific peptides.

The present application also provides an immunogenic composition comprising at least one nucleic acid encoding a disease-specific peptide, wherein said disease-specific peptide is identified by any of the methods described herein. In some embodiments, the immunogenic composition comprises a plurality of nucleic acids each encoding at least one disease-specific peptide. In some embodiments, the immunogenic composition comprising a nucleic acid encoding two or more (such as any of 3, 4, 5, 6, 7, 8, 9, or more) disease-specific peptides.

The present application in yet another aspect also provides a method of stimulating an immune response in an individual with a disease comprising administering any immunogenic compositions described herein. In some embodiments, the method further comprises administering another agent. In some embodiments, the other agent is an immunomodulator. In some embodiments, the other agent is a checkpoint protein. In some embodiments, the other agent is an antagonist of PD-1 (such as an anti-PD1 antibody). In some embodiments, the other agent is an antagonist of PD-L1 (such as an anti-PD-L1 antibody).

The present application in yet another aspect also provides a method of stimulating an immune response in an individual with a disease comprising: a) identifying a disease-specific immunogenic mutant peptide from a disease tissue in the individual according to any one of the identification method described above; b) producing a composition comprising a peptide or a nucleic acid encoding the peptide based on the sequence of the identified disease-specific immunogenic mutant peptide; c) administering the composition to the individual. In some embodiments, the method further comprises administering a PD-1 antagonist (such as anti-PD1 antibody) to the individual. In some embodiments, the method further comprises administering a PD-L1 antagonist (such as anti-PD-L1 antibody) to the individual.

DETAILED DESCRIPTION OF THE INVENTION

Figure 1:
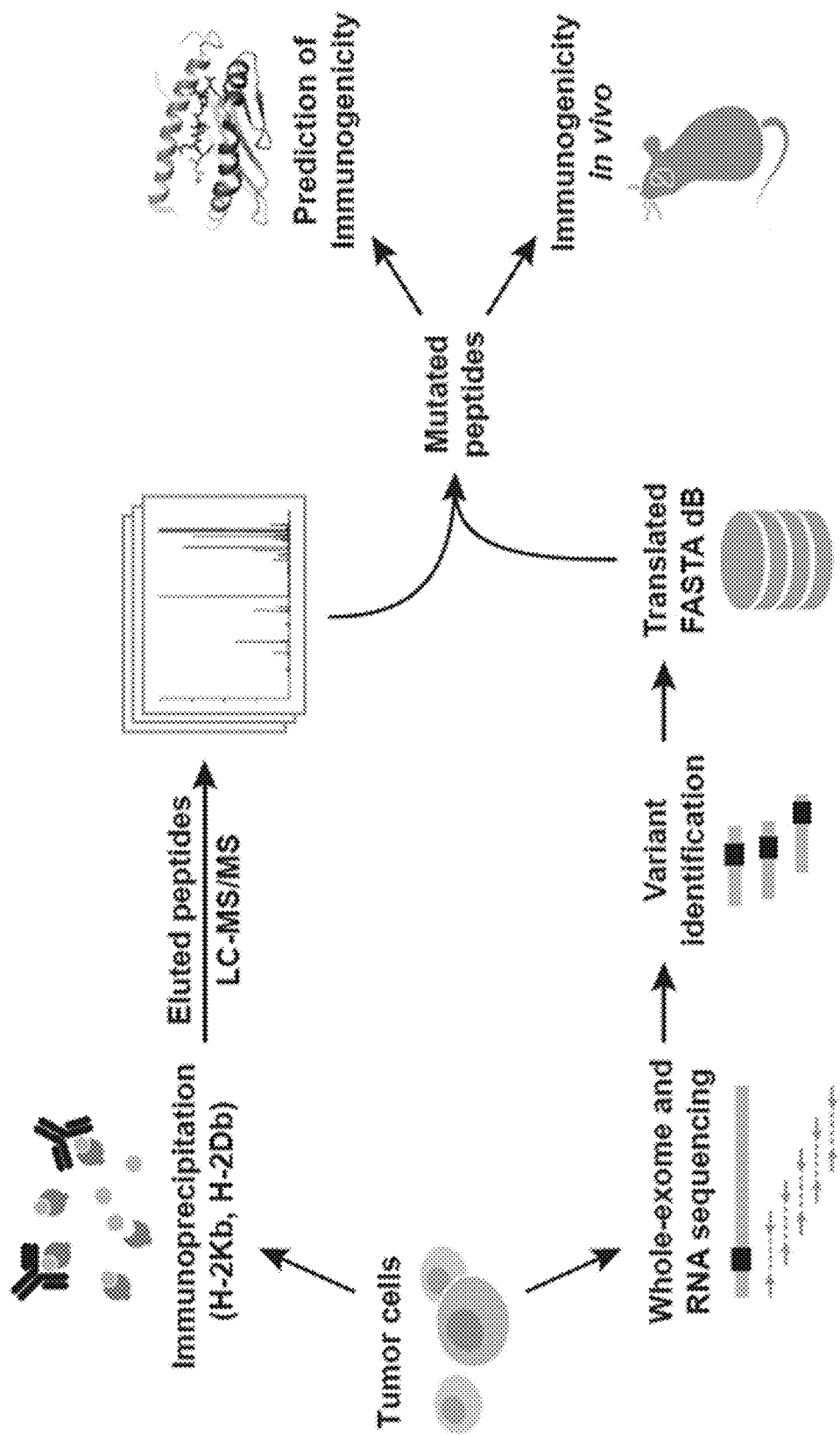
FIG. 1 illustrates exemplary methods of immunogenic peptide identification.

The present application provides high-efficiency screening platforms for identifying disease-specific immunogenic mutant peptides. By combining sequence-based variant identification methods with immunogenicity prediction and/or mass spectrometry, the methods described herein allow powerful and efficient identification of disease-specific immunogenic mutant peptides from the disease tissue (such as tumor cells) of an individual. These peptides, or nucleotide-based precursors (e.g., DNA or RNA), can be useful for a variety of different applications, such as development of vaccines, development of mutant peptide-specific therapeutics (such as antibody therapeutics or T-cell receptor ("TCR")-based therapeutics), as well as development of tools for monitoring the kinetics and distribution of T cell responses. For example, individual peptide or peptide collections can be utilized to do comparative binding affinity measurements or multimerized to measure antigen-specific T cell responses by MHC multimer flow cytometry. The methods described herein are particularly useful in the context of personalized medicine, where mutant peptides identified from a diseased individual can be used for developing therapeutics (e.g., peptide-, DNA-, or RNA-based vaccines) for treating the same individual.

Thus, the present application in one aspect provides a method of identifying a disease-specific immunogenic mutant peptide from a disease tissue of an individual by combining sequence-based variant identification methods with immunogenicity prediction.

In another aspect, the present application provides a method of identifying a disease-specific immunogenic mutant peptide from a diseased tissue of an individual by combining sequence-based variant identification methods with mass spectrometry.

Also provided are kits and systems useful for the methods described herein. Further included are immunogenic composition comprising peptides, cells presenting such peptides, and nucleic acids encoding such peptides identified.

Definitions

As used in this disclosure, the singular forms "a," "an," and "the" specifically also encompass the plural forms of the terms to which they refer, unless the content clearly dictates otherwise. Reference to "about" a value or parameter herein includes (and describes) variations that are directed to that value or parameter per se. For example, description referring to "about X" includes description of "X".

It is understood that aspects and embodiments of the invention described herein include "consisting" and/or "consisting essentially of" aspects and embodiments.

As used herein, "disease-specific mutant peptide" refers to a peptide that comprises at least one mutated amino acid present in a disease tissue but not in a normal tissue. "Disease-specific immunogenic mutant peptide" refers to a disease-specific mutant peptide that is capable of provoking an immune response in an individual. Disease-specific mutant peptides can arise from, for example: non-synonymous mutations leading to different amino acids in the protein (e.g., point mutations); read-through mutations in which a stop codon is modified or deleted, leading to translation of a longer protein with a novel tumor-specific sequence at the C-terminus; splice site mutations that lead to the inclusion of an intron in the mature mRNA and thus a unique tumor-specific protein sequence; chromosomal rearrangements that give rise to a chimeric protein with tumor-specific sequences at the junction of 2 proteins (i.e., gene fusion); and frameshift mutations or deletions that lead to a new open reading frame with a novel tumor-specific protein sequence. See, e.g., Sensi and Anichini, *Clin Cancer Res*, 2006, v. 12, 5023-5032.

A "variant-coding sequence" as used herein refers to a sequence having a variation compared to a sequence in a reference sample, wherein the sequence variation results in a change in an amino acid sequence contained in or encoded by the variant-coding sequence. The variant-coding sequence can be a nucleic acid sequence having a mutation that results in an amino acid change in the encoded amino acid sequence. Alternatively, the variant-coding sequence can be an amino acid sequence containing an amino acid mutation.

"Expression variant-coding sequence" refers to variant-coding sequences that are expressed in the disease tissue of the individual.

A nucleic acid sequence "encoding" a peptide refers to a nucleic acid containing the coding sequence for the peptide. An amino acid sequence "encoding" a peptide refers to an amino acid sequence containing the sequence of the peptide.

An "epitope variant-coding sequence" refers to a variant-coding sequence that encodes a peptide that binds or is predicted to bind to an MHC molecule (such as MHC class I molecule, or MHCI).

An "immunogenic variant-coding sequence" refers to a variant-coding sequence that encodes a peptide that is predicted to be immunogenic.

As used herein, the term "disease tissue" refers to the tissue associated with the disease in an individual, and includes a plurality of cells. "Disease tissue sample" refers to a sample of the disease tissue.

"Peptide precursor" used herein refers to a polypeptide present in the disease tissue of an individual that comprises the peptide of interest. For example, the peptide precursor may be a polypeptide present in the disease tissue that can be process by an immunoproteasome to produce the peptide of interest.

Methods of Identifying Immunogenic Mutant Peptides

The methods of the present application in one aspect combine sequence-specific variant identification methods with methods of immunogenicity prediction. For example, in some embodiments, there is provided a method of identifying a disease-specific immunogenic mutant peptide from a disease tissue in an individual, comprising: a) providing a first set of variant-coding sequences of the disease tissue in the individual, each variant-coding sequence having a variation in the sequence compared to a reference sample; and b) selecting immunogenic variant-coding sequences from the first set of variant-coding sequences, wherein the selecting step comprises predicting immunogenicity of the peptides comprising a variant amino acid encoded by the variant-coding sequences, thereby identifying the disease-specific immunogenic mutant peptide. In some embodiments, there is provided a method of identifying a disease-specific immunogenic mutant peptide from a disease tissue in an individual that serves as a neoepitope in a disease tissue. In some embodiments, the set of variant-coding sequences comprises more than 1, 10, 100, 1,000, or 10,000 different variant-coding sequences. In some embodiments, there is provided a method of identifying a disease-specific immunogenic mutant peptide from a disease tissue in an individual, comprising: a) obtaining a first set of variant-coding sequences of the disease tissue in the individual, each variant-coding sequence having a variation in the sequence compared to a reference sample; and b) selecting immunogenic variant-coding sequences from the first set of variant-coding sequences, wherein the selecting step comprises predicting immunogenicity of the peptides comprising a variant amino acid encoded by the variant-coding sequences, thereby identifying the disease-specific immunogenic mutant peptide. In some embodiments, the selecting step comprises predicting immunogenicity of the peptides based on one or more (such as any of 2, 3, 4, 5, 6, 7, 8, 9, 10, or 11) parameters: i) binding affinity of the peptide to the MHCI molecule; ii) protein level of a peptide precursor containing the peptide; iii) expression level of the transcript encoding the peptide precursor; iv) processing efficiency of the peptide precursor by an immunoproteasome; v) timing of the expression of the transcript encoding the peptide precursor; vi) binding affinity of the peptide to a TCR molecule; vii) position of a variant amino acid within the peptide; viii) solvent exposure of the peptide when bound to a MHCI molecule; ix) solvent exposure of the variant amino acid when bound to a MHCI molecule; x) content of aromatic residues in the peptide; xi) properties of the variant amino acid when compared to the wild type residue (e.g., variation from charged to hydrophobic or vice versa); and xii) nature of the peptide precursor.

In some embodiments, the first set of variant-coding sequences can first be filtered to obtain a smaller set of variant-coding sequences encoding peptides predicted to bind an MHC molecule (referred to as "epitope variant-coding sequences"), and the smaller set of variant-coding sequences are then subjected to selection based on prediction of immunogenicity. In such embodiments, the method may comprise: a) providing a first set of variant-coding sequences of the disease tissue in the individual, each variant-coding sequence having a variation in the sequence compared to a reference sample; b) selecting a second set of epitope variant-coding sequences from the first set based on predicted ability of the peptides encoded by the first set of variant-coding sequences to bind to an MHC molecule (such as MHC class I molecule, or MHCI), and c) selecting immunogenic variant-coding sequences from the second set of epitope variant-coding sequences, wherein the selecting step comprises predicting immunogenicity of the peptides comprising a variant amino acid encoded by the epitope variant-coding sequences, thereby identifying the disease-specific immunogenic mutant peptide. In some embodiments, the method comprises: a) obtaining a first set of variant-coding sequences of the disease tissue in the individual, each variant-coding sequence having a variation in the sequence compared to a reference sample; b) selecting a second set of epitope variant-coding sequences from the first set based on predicted ability of the peptides encoded by the first set of variant-coding sequences to bind to an MHC molecule (such as MHC class I molecule, or MHCI), and c) selecting immunogenic variant-coding sequences from the second set of epitope variant-coding sequences, wherein the selecting step comprises predicting immunogenicity of the peptides comprising a variant amino acid encoded by the epitope variant-coding sequences, thereby identifying the disease-specific immunogenic mutant peptide. In some embodiments, the method further comprises validating the disease-specific immunogenic mutant peptides by functional analysis. In some embodiments, the disease is cancer. In some embodiments, the individual is a human individual (such as a human individual having cancer).

In some embodiments, there is provided a method of identifying a disease-specific immunogenic mutant peptide from a disease tissue in an individual, comprising: a) obtaining a first set of variant-coding sequences of the disease tissue in the individual based on the genomic sequence of the disease tissue in the individual, each variant-coding sequence having a variation in the sequence compared to a reference sample; and b) selecting immunogenic variant-coding sequences from the first set of variant-coding sequences, wherein the selecting step comprises predicting immunogenicity of the peptides comprising a variant amino acid encoded by the variant-coding sequences, thereby identifying the disease-specific immunogenic mutant peptide. In some embodiments, the genomic sequence is obtained by whole-genome sequencing. In some embodiments, the genomic sequence is obtained by whole-exome sequencing. In some embodiments, the genomic sequence is obtained by targeted-genome or exome sequencing. For example, the genomic sequences in the disease tissue and/or reference sample can first be enriched by a set of probes (for example probes specific for disease-associated genes) before being processed for variant identification. In some embodiments, the first set of variant-coding sequences can be first filtered to obtain a smaller set of epitope variant-coding sequences, and the smaller set of variant-coding sequences is then subjected to selection based on prediction of immunogenicity. For example, in some embodiments, there is provided a method of identifying a disease-specific immunogenic mutant peptide from a disease tissue in an individual, comprising: a) obtaining a first set of variant-coding sequences of the disease tissue in the individual based on the genomic sequence of the disease tissue in the individual, each variant-coding sequence having a variation in the sequence compared to a reference sample; b) selecting a second set of epitope variant-coding sequences from the first set based on predicted ability of the peptides encoded by the first set of variant-coding sequences to bind to an MHC molecule (such as MHC class I molecule, or MHCI), and c) selecting immunogenic variant-coding sequences from the second set of epitope variant-coding sequences, wherein the selecting step comprises predicting immunogenicity of the peptides comprising a variant amino acid encoded by the epitope variant-coding sequences, thereby identifying the disease-specific immunogenic mutant peptide. In some embodiments, the method further comprises validating the disease-specific immunogenic mutant peptides by functional analysis. In some embodiments, the disease is cancer. In some embodiments, the individual is a human individual (such as a human individual having cancer).

In some embodiments, there is provided a method of identifying a disease-specific immunogenic mutant peptide from a disease tissue in an individual, comprising: a) obtaining a first set of variant-coding sequences of the disease tissue in the individual based on the transcriptome sequence of the disease tissue in the individual, each variant-coding sequence having a variation in the sequence compared to a reference sample; and b) selecting immunogenic variant-coding sequences from the first set of variant-coding sequences, wherein the selecting step comprises predicting immunogenicity of the peptides comprising a variant amino acid encoded by the variant-coding sequences, thereby identifying the disease-specific immunogenic mutant peptide. In some embodiments, the transcriptome sequence is obtained by whole-transcriptome RNA-Seq sequencing. In some embodiments, the transcription sequence is obtained by targeted-transcriptome sequencing. For example, the RNA or cDNA sequences in the disease tissue and/or reference sample can first be enriched by a set of probes (for example probes specific for disease-associated genes) before being processed for variant identification. In some embodiments, the first set of variant-coding sequences can first be filtered to obtain a smaller set of epitope variant-coding sequences, and the smaller set of variant-coding sequences is then subjected to prediction of immunogenicity. For example, in some embodiments, there is provided a method of identifying a disease-specific immunogenic mutant peptide from a disease tissue in an individual, comprising: a) obtaining a first set of variant-coding sequences of the disease tissue in the individual based on the transcriptome sequence of the disease tissue in the individual, each variant-coding sequence having a variation in the sequence compared to a reference sample; b) selecting a second set of epitope variant-coding sequences from the first set based on predicted ability of the peptides encoded by the first set of epitope variant-coding sequences to bind to an MHC molecule (such as MHC class I molecule, or MHCI), and c) selecting immunogenic variant-coding sequences from the second set of variant-coding sequences, wherein the selecting step comprises predicting immunogenicity of the peptides comprising a variant amino acid encoded by the epitope variant-coding sequences, thereby identifying the disease-specific immunogenic mutant peptide.

In some embodiments, there is provided a method of identifying a disease-specific immunogenic mutant peptide from a disease tissue in an individual, comprising: a) providing a first set of variant-coding sequences of the disease tissue in the individual based on the genomic sequence of the disease tissue in the individual, each variant-coding sequence having a variation in the sequence compared to a reference sample; b) selecting a second set of expression variant-coding sequences from the first set based on the transcriptomic sequences of the disease tissue in the individual; and c) selecting immunogenic variant-coding sequences from the second set of expression variant-coding sequences, wherein the selecting step comprises predicting immunogenicity of the peptides comprising a variant amino acid encoded by the expression variant-coding sequences, thereby identifying the disease-specific immunogenic mutant peptide. In some embodiments, the method comprises: a) obtaining a first set of variant-coding sequences of the disease tissue in the individual based on the genomic sequence of the disease tissue in the individual, each variant-coding sequence having a variation in the sequence compared to a reference sample; b) selecting a second set of expression variant-coding sequences from the first set based on the transcriptomic sequences of the disease tissue in the individual; and c) selecting immunogenic variant-coding sequences from the second set of expression variant-coding sequences, wherein the selecting step comprises predicting immunogenicity of the peptides comprising a variant amino acid encoded by the expression variant-coding sequences, thereby identifying the disease-specific immunogenic mutant peptide.

In some embodiments, the second set of expression variant-coding sequences can be filtered to obtain a smaller set of epitope variant-coding sequences, and the smaller set of variant-coding sequences is then subjected to prediction of immunogenicity. Thus, for example, in some embodiments, there is provided a method of identifying a disease-specific immunogenic mutant peptide from a disease tissue in an individual, comprising: a) providing a first set of variant-coding sequences of the disease tissue in the individual based on the genomic sequence of the disease tissue in the individual, each variant-coding sequence having a variation in the sequence compared to a reference sample; b) selecting a second set of expression variant-coding sequences from the first set based on the transcriptomic sequences of the disease tissue in the individual; c) selecting a third set of epitope variant-coding sequences from the second set based on predicted ability of the peptides encoded by the second set of expression variant-coding sequences to bind to an MHC molecule (such as MHC class I molecule, or MHCI), and d) selecting immunogenic variant-coding sequences from the third set of epitope variant-coding sequences, wherein the selecting step comprises predicting immunogenicity of the peptides comprising a variant amino acid encoded by the epitope variant-coding sequences, thereby identifying the disease-specific immunogenic mutant peptide. In some embodiments, the method comprises: a) obtaining a first set of variant-coding sequences of the disease tissue in the individual based on the genomic sequence of the disease tissue in the individual, each variant-coding sequence having a variation in the sequence compared to a reference sample; b) selecting a second set of expression variant-coding sequences from the first set based on the transcriptomic sequences of the disease tissue in the individual; c) selecting a third set of epitope variant-coding sequences from the second set based on predicted ability of the peptides encoded by the second set of expression variant-coding sequences to bind to an MHC molecule (such as MHC class I molecule, or MHCI), and d) selecting immunogenic variant-coding sequences from the third set of epitope variant-coding sequences, wherein the selecting step comprises predicting immunogenicity of the peptides comprising a variant amino acid encoded by the epitope variant-coding sequences, thereby identifying the disease-specific immunogenic mutant peptide. In some embodiments, the method further comprises validating the disease-specific immunogenic mutant peptides by functional analysis. In some embodiments, the disease is cancer. In some embodiments, the individual is a human individual (such as a human individual having cancer).

In some embodiments, the disease-specific immunogenic mutant peptides identified by the methods described herein are further validated by correlating the variant-coding sequence information with information of peptides physically bound to an MHC molecule. The methods for example can further comprise: obtaining a plurality of peptides that are bound to an MHC molecule from the disease tissue; subjecting the MHC-bound peptides to mass spectrometry-based sequencing; and correlating the mass spectrometry-derived sequence information of the MHC-bound peptides with the peptides predicted to be immunogenic variant-coding sequences. The mass-spectrometry and correlation methods are further described in sections below.

In another aspect, there are provided methods which combine sequence-specific variant identification method with mass spectrometry analysis. For example, in some embodiments, there is provided a method of identifying a disease-specific immunogenic mutant peptide from a disease tissue in an individual, comprising: a) obtaining a plurality of peptides that are bound to an MHC molecule from a diseased tissue of an individual; b) subjecting the MHC-bound peptides to mass spectrometry-based sequencing; and c) correlating the mass spectrometry-derived sequence information of the MHC-bound peptides with a set of variant-coding sequences of the disease tissue in the individual, each variant-coding sequence having a variation in the sequence compared to a reference sample, thereby identifying the disease-specific immunogenic mutant peptide. In some embodiments, the plurality of peptides bound to MHC are obtained by isolating MHC/peptide complexes (for example by immunoprecipitation) from the disease tissue and eluting the peptides from the MHC. In some embodiments, the peptides are subjected to tandem mass spectrometry. In some embodiments, the mass spectrometry-based sequencing comprises subjecting the peptides to mass spectrometry and comparing the mass spectrometry spectra with reference spectra (such as hypothetical mass spectrometry spectra of putative proteins encoded by sequences in a reference sample). In some embodiments, the mass spectrometry sequence information is filtered by peptide length and/or the presence of anchor motifs prior to the correlation step. In some embodiments, the method further comprises validating the disease-specific immunogenic mutant peptides by functional analysis. In some embodiments, the disease is cancer. In some embodiments, the individual is a human individual (such as a human individual having cancer).

In some embodiments, there is provided a method of identifying a disease-specific immunogenic mutant peptide from a disease tissue in an individual, comprising: a) obtaining a first set of variant-coding sequences of the disease tissue in the individual, each variant-coding sequence having a variation in the sequence compared to a reference sample; b) obtaining a plurality of peptides that are bound to an MHC molecule from a diseased tissue of an individual; c) subjecting the MHC-bound peptides to mass spectrometry-based sequencing; and d) correlating the mass spectrometry-derived sequence information of the MHC-bound peptides with the first set of variant-coding sequences, thereby identifying the disease-specific immunogenic mutant peptide. In some embodiments, the first set of variant-coding sequences can be filtered to obtain a smaller set of variant-coding sequences encoding peptides that is predicted to bind an MHC molecule (hereinafter referred to as "epitope variant-coding sequences"), and the smaller set of variant-coding sequences is then subjected to the correlation analysis. In such embodiments, the method may comprise: a) providing a first set of variant-coding sequences of the disease tissue in the individual, each variant-coding sequence having a variation in the sequence compared to a reference sample; b) selecting a second set of epitope variant-coding sequences from the first set based on predicted ability of the peptides encoded by the first set of variant-coding sequences to bind to an MHC molecule (such as MHC class I molecule, or MHCI), c) obtaining a plurality of peptides that are bound to an MHC molecule from a diseased tissue of an individual; d) subjecting the MHC-bound peptides to mass spectrometry-based sequencing; and e) correlating the mass spectrometry-derived sequence information of the MHC-bound peptides with the second set of epitope variant-coding sequences, thereby identifying the disease-specific immunogenic mutant peptide. In some embodiments, the method comprises: a) obtaining a first set of variant-coding sequences of the disease tissue in the individual, each variant-coding sequence having a variation in the sequence compared to a reference sample; b) selecting a second set of epitope variant-coding sequences from the first set based on predicted ability of the peptides encoded by the first set of variant-coding sequences to bind to an MHC molecule (such as MHC class I molecule, or MHCI), c) obtaining a plurality of peptides that are bound to an MHC molecule from a diseased tissue of an individual; d) subjecting the MHC-bound peptides to mass spectrometry-based sequencing; and e) correlating the mass spectrometry-derived sequence information of the MHC-bound peptides with the second set of epitope variant-coding sequences, thereby identifying the disease-specific immunogenic mutant peptide. In some embodiments, the method further comprises validating the disease-specific immunogenic mutant peptides by functional analysis. In some embodiments, the disease is cancer. In some embodiments, the individual is a human individual (such as a human individual having cancer).

In some embodiments, there is provided a method of identifying a disease-specific immunogenic mutant peptide from a disease tissue in an individual, comprising: a) obtaining a first set of variant-coding sequences of the disease tissue in the individual based on the genomic sequence of the disease tissue in the individual, each variant-coding sequence having a variation in the sequence compared to a reference sample; b) obtaining a plurality of peptides that are bound to an MHC molecule from a diseased tissue of an individual; c) subjecting the MHC-bound peptides to mass spectrometry-based sequencing; and d) correlating the mass spectrometry-derived sequence information of the MHC-bound peptides with the first set of variant-coding sequences, thereby identifying the disease-specific immunogenic mutant peptide. In some embodiments, the genomic sequence is obtained by whole-genome sequencing. In some embodiments, the genomic sequence is obtained by whole-exome sequencing. In some embodiments, the genomic sequence is obtained by targeted-genome or exome sequencing. For example, the genomic sequences in the disease tissue and/or reference sample can be first be enriched by a set of probes (for example probes specific for disease-associated genes) before being processed for variant identification.

In some embodiments, the first set of variant-coding sequences can be filtered to obtain a smaller set of variant-coding sequences encoding peptides that is predicted to bind an MHC molecule (hereinafter referred to as "epitope variant-coding sequences"), and the smaller set of variant-coding sequences is then subjected to prediction of immunogenicity. For example, in some embodiments, there is provided a method of identifying a disease-specific immunogenic mutant peptide from a disease tissue in an individual, comprising: a) obtaining a first set of variant-coding sequences of the disease tissue in the individual based on the genomic sequence of the disease tissue in the individual, each variant-coding sequence having a variation in the sequence compared to a reference sample; b) selecting a second set of epitope variant-coding sequences from the first set based on predicted ability of the peptides encoded by the first set of variant-coding sequences to bind to an MHC molecule (such as MHC class I molecule, or MHCI), c) obtaining a plurality of peptides that are bound to an MHC molecule from a diseased tissue of an individual; d) subjecting the MHC-bound peptides to mass spectrometry-based sequencing; and e) correlating the mass spectrometry-derived sequence information of the MHC-bound peptides with the second set of epitope variant-coding sequences, thereby identifying the disease-specific immunogenic mutant peptide.

In some embodiments, there is provided a method of identifying a disease-specific immunogenic mutant peptide from a disease tissue in an individual, comprising: a) obtaining a first set of variant-coding sequences of the disease tissue in the individual based on the transcriptome sequence of the disease tissue in the individual, each variant-coding sequence having a variation in the sequence compared to a reference sample; b) obtaining a plurality of peptides that are bound to an MHC molecule from a diseased tissue of an individual; c) subjecting the MHC-bound peptides to mass spectrometry-based sequencing; and d) correlating the mass spectrometry-derived sequence information of the MHC-bound peptides with the first set of variant-coding sequences, thereby identifying the disease-specific immunogenic mutant peptide In some embodiments, the transcriptome sequence is obtained by whole-transcriptome RNA-Seq sequencing. In some embodiments, the transcriptome sequence is obtained by targeted-transcriptome sequencing. For example, the RNA sequences or cDNA sequences in the disease tissue and/or reference sample can first be enriched by a set of probes (for example probes specific for disease-associated genes) before being processed for variant identification. In some embodiments, the first set of variant-coding sequences can be filtered to obtain a smaller set of epitope variant-coding sequences, and the smaller set of variant-coding sequences are then subjected to prediction of immunogenicity. For example, in some embodiments, there is provided a method of identifying a disease-specific immunogenic mutant peptide from a disease tissue in an individual, comprising: a) obtaining a first set of variant-coding sequences of the disease tissue in the individual based on the transcriptome sequence of the disease tissue in the individual, each variant-coding sequence having a variation in the sequence compared to a reference sample; b) selecting a second set of epitope variant-coding sequences from the first set based on predicted ability of the peptides encoded by the first set of variant-coding sequences to bind to an MHC molecule (such as MHC class I molecule, or MHCI), c) obtaining a plurality of peptides that are bound to an MHC molecule from a diseased tissue of an individual; d) subjecting the MHC-bound peptides to mass spectrometry-based sequencing; and e) correlating the mass spectrometry-derived sequence information of the MHC-bound peptides with the second set of epitope variant-coding sequences, thereby identifying the disease-specific immunogenic mutant peptide.

In some embodiments, there is provided a method of identifying a disease-specific immunogenic mutant peptide from a disease tissue in an individual, comprising: a) providing a first set of variant-coding sequences of the disease tissue in the individual based on the genomic sequence of the disease tissue in the individual, each variant-coding sequence having a variation in the sequence compared to a reference sample; b) selecting a second set of expression variant-coding sequences from the first set based on the transcriptomic sequences of the disease tissue in the individual; c) obtaining a plurality of peptides that are bound to an MHC molecule from a diseased tissue of an individual; d) subjecting the MHC-bound peptides to mass spectrometry-based sequencing; and e) correlating the mass spectrometry-derived sequence information of the MHC-bound peptides with the second set of expression variant-coding sequences, thereby identifying the disease-specific immunogenic mutant peptide. In some embodiments, the method comprises: a) obtaining a first set of variant-coding sequences of the disease tissue in the individual based on the genomic sequence of the disease tissue in the individual, each variant-coding sequence having a variation in the sequence compared to a reference sample; b) selecting a second set of expression variant-coding sequences from the first set based on the transcriptomic sequences of the disease tissue in the individual; c) obtaining a plurality of peptides that are bound to an MHC molecule from a diseased tissue of an individual; d) subjecting the MHC-bound peptides to mass spectrometry-based sequencing; and e) correlating the mass spectrometry-derived sequence information of the MHC-bound peptides with the second set of expression variant-coding sequences, thereby identifying the disease-specific immunogenic mutant peptide.

In some embodiments, the second set of expression variant-coding sequences can be filtered to obtain a smaller set of epitope variant-coding sequences, and the smaller set of variant-coding sequences is then subjected to prediction of immunogenicity. Thus, for example, in some embodiments, there is provided a method of identifying a disease-specific immunogenic mutant peptide from a disease tissue in an individual, comprising: a) providing a first set of variant-coding sequences of the disease tissue in the individual based on the genomic sequence of the disease tissue in the individual, each variant-coding sequence having a variation in the sequence compared to a reference sample; b) selecting a second set of expression variant-coding sequences from the first set based on the transcriptomic sequences of the disease tissue in the individual; c) selecting a third set of epitope variant-coding sequences from the second set based on predicted ability of the peptides encoded by the second set of expression variant-coding sequences to bind to an MHC molecule (such as MHC class I molecule, or MHCI), d) obtaining a plurality of peptides that are bound to an MHC molecule from a diseased tissue of an individual; e) subjecting the MHC-bound peptides to mass spectrometry-based sequencing; and f) correlating the mass spectrometry-derived sequence information of the MHC-bound peptides with the third set of epitope variant-coding sequences, thereby identifying the disease-specific immunogenic mutant peptide. In some embodiments, the method comprises: a) obtaining a first set of variant-coding sequences of the disease tissue in the individual based on the genomic sequence of the disease tissue in the individual, each variant-coding sequence having a variation in the sequence compared to a reference sample; b) selecting a second set of expression variant-coding sequences from the first set based on the transcriptomic sequences of the disease tissue in the individual; c) selecting a third set of epitope variant-coding sequences from the second set based on predicted ability of the peptides encoded by the second set of expression variant-coding sequences to bind to an MHC molecule (such as MHC class I molecule, or MHCI), d) obtaining a plurality of peptides that are bound to an MHC molecule from a diseased tissue of an individual; e) subjecting the MHC-bound peptides to mass spectrometry-based sequencing; and f) correlating the mass spectrometry-derived sequence information of the MHC-bound peptides with the third set of epitope variant-coding sequences, thereby identifying the disease-specific immunogenic mutant peptide. In some embodiments, the method further comprises validating the disease-specific immunogenic mutant peptides by functional analysis. In some embodiments, the disease is cancer. In some embodiments, the individual is a human individual (such as a human individual having cancer).

In some embodiments, the disease-specific immunogenic mutant peptides identified by the mass-spectrometry based methods described herein are further selected by predicting immunogenicity of the peptides. In some embodiments, the selecting step comprises predicting immunogenicity of the peptides based on one or more (such as any of 2, 3, 4, 5, 6, 7, 8, 9, 10, or 11) parameters: i) binding affinity of the peptide to the MHCI molecule; ii) protein level of a peptide precursor containing the peptide; iii) expression level of the transcript encoding the peptide precursor; iv) processing efficiency of the peptide precursor by an immunoproteasome; v) timing of the expression of the transcript encoding the peptide precursor; vi) binding affinity of the peptide to a TCR molecule; vii) position of a variant amino acid within the peptide; viii) solvent exposure of the peptide when bound to a MHCI molecule; ix) solvent exposure of the variant amino acid when bound to a MHCI molecule; x) content of aromatic residues in the peptide; and xi) nature of the peptide precursor.

Thus, for example, in some embodiments, there is provided a method of identifying a disease-specific immunogenic mutant peptide from a disease tissue in an individual, comprising: a) obtaining a plurality of peptides that are bound to an MHC molecule from a diseased tissue of an individual; b) subjecting the MHC-bound peptides to mass spectrometry-based sequencing; and c) correlating the mass spectrometry-derived sequence information of the MHC-bound peptides with a set of variant-coding sequences of the disease tissue in the individual, each variant-coding sequence having a variation in the sequence compared to a reference sample to obtain a second set of variant-coding sequences, and d) selecting immunogenic variant-coding sequences from the second set of variant-coding sequences, wherein the selecting step comprises predicting immunogenicity of the peptides comprising a variant amino acid encoded by the second set of variant-coding sequences, thereby identifying the disease-specific immunogenic mutant peptide. In some embodiments, there is provided a method of identifying a disease-specific immunogenic mutant peptide from a disease tissue in an individual, comprising: a) obtaining a set of variant-coding sequences of the disease tissue in the individual, each variant-coding sequence having a variation in the sequence compared to a reference sample; b) obtaining a plurality of peptides that are bound to an MHC molecule from a diseased tissue of an individual; c) subjecting the MHC-bound peptides to mass spectrometry-based sequencing; d) correlating the mass spectrometry-derived sequence information of the MHC-bound peptides with the first set of variant-coding sequences to obtain a second set of variant-coding sequences, and e) selecting immunogenic variant-coding sequences from the second set of variant-coding sequences, wherein the selecting step comprises predicting immunogenicity of the peptides comprising a variant amino acid encoded by the second set of variant-coding sequences, thereby identifying the disease-specific immunogenic mutant peptide. In some embodiments, the method comprises: a) providing a first set of variant-coding sequences of the disease tissue in the individual, each variant-coding sequence having a variation in the sequence compared to a reference sample; b) selecting a second set of epitope variant-coding sequences from the first set based on predicted ability of the peptides encoded by the first set of variant-coding sequences to bind to an MHC molecule (such as MHC class I molecule, or MHCI), c) obtaining a plurality of peptides that are bound to an MHC molecule from a diseased tissue of an individual; d) subjecting the MHC-bound peptides to mass spectrometry-based sequencing; e) correlating the mass spectrometry-derived sequence information of the MHC-bound peptides with the second set of epitope variant-coding sequences to obtain a third set of variant-coding sequences, and f) selecting immunogenic variant-coding sequences from the third set of variant-coding sequences, wherein the selecting step comprises predicting immunogenicity of the peptides comprising a variant amino acid encoded by the third set of variant-coding sequences, thereby identifying the disease-specific immunogenic mutant peptide. In some embodiments, the method comprises: a) obtaining a first set of variant-coding sequences of the disease tissue in the individual, each variant-coding sequence having a variation in the sequence compared to a reference sample; b) selecting a second set of epitope variant-coding sequences from the first set based on predicted ability of the peptides encoded by the first set of variant-coding sequences to bind to an MHC molecule (such as MHC class I molecule, or MHCI), c) obtaining a plurality of peptides that are bound to an MHC molecule from a diseased tissue of an individual; d) subjecting the MHC-bound peptides to mass spectrometry-based sequencing; and e) correlating the mass spectrometry-derived sequence information of the MHC-bound peptides with the set of epitope variant-coding sequences to obtain a third set of variant-coding sequences, and f) selecting immunogenic variant-coding sequences from the third set of variant-coding sequences, wherein the selecting step comprises predicting immunogenicity of the peptides comprising a variant amino acid encoded by the third set of variant-coding sequences, thereby identifying the disease-specific immunogenic mutant peptide. In some embodiments, the method further comprises validating the disease-specific immunogenic mutant peptides by functional analysis. In some embodiments, the method further comprises validating the disease-specific immunogenic mutant peptides by functional analysis. In some embodiments, the disease is cancer. In some embodiments, the individual is a human individual (such as a human individual having cancer).

In some embodiments, there is provided a method of identifying a disease-specific immunogenic mutant peptide from a disease tissue in an individual, comprising: a) providing a first set of variant-coding sequences of the disease tissue in the individual based on the genomic sequence of the disease tissue in the individual, each variant-coding sequence having a variation in the sequence compared to a reference sample; b) selecting a second set of expression variant-coding sequences from the first set based on the transcriptomic sequences of the disease tissue in the individual; c) obtaining a plurality of peptides that are bound to an MHC molecule from a diseased tissue of an individual; d) subjecting the MHC-bound peptides to mass spectrometry-based sequencing; and e) correlating the mass spectrometry-derived sequence information of the MHC-bound peptides with the second set of expression variant-coding sequences to obtain a third set of variant-coding sequences, and f) selecting immunogenic variant-coding sequences from the third set of variant-coding sequences, wherein the selecting step comprises predicting immunogenicity of the peptides comprising a variant amino acid encoded by the third set of variant-coding sequences, thereby identifying the disease-specific immunogenic mutant peptide. In some embodiments, the method comprises: a) obtaining a first set of variant-coding sequences of the disease tissue in the individual based on the genomic sequence of the disease tissue in the individual, each variant-coding sequence having a variation in the sequence compared to a reference sample; b) selecting a second set of expression variant-coding sequences from the first set based on the transcriptomic sequences of the disease tissue in the individual; c) obtaining a plurality of peptides that are bound to an MHC molecule from a diseased tissue of an individual; d) subjecting the MHC-bound peptides to mass spectrometry-based sequencing; and e) correlating the mass spectrometry-derived sequence information of the MHC-bound peptides with the second set of expression variant-coding sequences to obtain a third set of variant-coding sequences, and f) selecting immunogenic variant-coding sequences from the third set of variant-coding sequences, wherein the selecting step comprises predicting immunogenicity of the peptides comprising a variant amino acid encoded by the third set of variant-coding sequences, thereby identifying the disease-specific immunogenic mutant peptide. In some embodiments, the method further comprises validating the disease-specific immunogenic mutant peptides by functional analysis. In some embodiments, the disease is cancer. In some embodiments, the individual is a human individual (such as a human individual having cancer).

In some embodiments, there is provided a method of identifying a disease-specific immunogenic mutant peptide from a disease tissue in an individual, comprising: a) providing a first set of variant-coding sequences of the disease tissue in the individual based on the genomic sequence of the disease tissue in the individual, each variant-coding sequence having a variation in the sequence compared to a reference sample; b) selecting a second set of expression variant-coding sequences from the first set based on the transcriptomic sequences of the disease tissue in the individual; c) selecting a third set of epitope variant-coding sequences from the second set based on predicted ability of the peptides encoded by the second set of expression variant-coding sequences to bind to an MHC molecule (such as MHC class I molecule, or MHCI), d) obtaining a plurality of peptides that are bound to an MHC molecule from a diseased tissue of an individual; e) subjecting the MHC-bound peptides to mass spectrometry-based sequencing; and f) correlating the mass spectrometry-derived sequence information of the MHC-bound peptides with the third set of epitope variant-coding sequences to obtain a fourth set of variant-coding sequences, and g) selecting immunogenic variant-coding sequences from the fourth set of variant-coding sequences, wherein the selecting step comprises predicting immunogenicity of the peptides comprising a variant amino acid encoded by the fourth set of variant-coding sequences, thereby identifying the disease-specific immunogenic mutant peptide. In some embodiments, the method comprises: a) obtaining a first set of variant-coding sequences of the disease tissue in the individual based on the genomic sequence of the disease tissue in the individual, each variant-coding sequence having a variation in the sequence compared to a reference sample; b) selecting a second set of expression variant-coding sequences from the first set based on the transcriptomic sequences of the disease tissue in the individual; c) selecting a third set of epitope variant-coding sequences from the second set based on predicted ability of the peptides encoded by the second set of expression variant-coding sequences to bind to an MHC molecule (such as MHC class I molecule, or MHCI), d) obtaining a plurality of peptides that are bound to an MHC molecule from a diseased tissue of an individual; e) subjecting the MHC-bound peptides to mass spectrometry-based sequencing; and f) correlating the mass spectrometry-derived sequence information of the MHC-bound peptides with the third set of epitope variant-coding sequences to obtain a fourth set of variant-coding sequences, and g) selecting immunogenic variant-coding sequences from the fourth set of variant-coding sequences, wherein the selecting step comprises predicting immunogenicity of the peptides comprising a variant amino acid encoded by the fourth set of variant-coding sequences, thereby identifying the disease-specific immunogenic mutant peptide. In some embodiments, the method further comprises validating the disease-specific immunogenic mutant peptides by functional analysis. In some embodiments, the disease is cancer. In some embodiments, the individual is a human individual (such as a human individual having cancer).

Also provided herein are disease-specific immunogenic mutant peptides obtained by any one of the methods described herein. The disease-specific immunogenic mutant peptides can be used, for example, to make a composition (such as a vaccine composition) for treating the disease. Alternatively, the disease-specific immunogenic mutant peptide can be used for producing mutant-peptide-specific therapeutics such as therapeutic antibodies.

The methods described herein are particularly useful in the personalized medicine context, where disease-specific, immunogenic mutant peptides obtained by any one of the methods described herein are used to develop therapeutics (such as vaccines or therapeutic antibodies) for the same individual. Thus, for example, in some embodiments, there is provided a method of treating a disease (such as cancer) in an individual, comprising: a) identifying a disease-specific, immunogenic mutant peptides in the individual; and b) synthesizing the peptide; and c) administering the peptide to the individual. In some embodiments, there is provided a method of treating a disease (such as cancer) in an individual, comprising: a) obtaining a disease tissue sample from the individual; b) identifying a disease-specific, immunogenic mutant peptides in the individual; and c) synthesizing the peptide; and d) administering the peptide to the individual. In some embodiments, there is provided a method of treating a disease (such as cancer) in an individual, comprising: a) identifying a disease-specific, immunogenic mutant peptide in the individual; b) producing an antibody (or a TCR analog, such as a soluble TCR) specifically recognizing the mutant peptide; and c) administering the peptide to the individual. In some embodiments, there is provided a method of treating a disease (such as cancer) in an individual, comprising: a) obtaining a disease tissue sample from the individual; b) identifying a disease-specific, immunogenic mutant peptide in the individual; c) producing an antibody (or a TCR analog, such as a soluble TCR) specifically recognizing the mutant peptide; and d) administering the peptide to the individual. In some embodiments, the identification step combines sequence-specific variant identification method with methods of immunogenicity prediction. In some embodiments, the identification step combines sequence-specific variant identification method with mass spectrometry. Any methods of identifying a disease-specific, immunogenic mutant peptide described herein can be used for the treatment methods described herein.

Obtaining Variant-Coding Sequences

The methods described herein in various embodiments comprise providing and/or obtaining variant-coding sequences. The variant coding sequences can generally be obtained, for example, by sequencing the genomic or RNA sequences in the disease tissue sample of the individual and comparing the sequences to those obtained from a reference sample.

In some embodiments, the disease tissue is blood. In some embodiments, the disease tissue is a solid tissue (such as solid tumor). In some embodiments, the disease tissue is a collection of cells (for example circulating cancer cells in the blood). In some embodiments, the disease tissue is a collection of lymphocytes. In some embodiments, the disease tissue is a collection of leukocytes. In some embodiments, the disease tissue is a collection of epithelial cells. In some embodiments, the disease tissue is connective tissue. In some embodiments, the disease tissue is a collection of germ cells and/or pluripotent cells. In some embodiments, the disease tissue is a collection of blast cells.

Suitable disease tissue samples include, but are not limited to, tumor tissue, normal tissue adjacent to the tumor, normal tissue distal to the tumor, or peripheral blood lymphocytes. In some embodiments, the disease tissue sample is a tumor tissue. In some embodiments, the disease tissue sample is a biopsy containing cancer cells, such as fine needle aspiration of cancer cells (e.g., pancreatic cancer cells) or laparoscopy obtained cancer cells (e.g., pancreatic cancer cells). In some embodiments, the biopsied cells are centrifuged into a pellet, fixed, and embedded in paraffin prior to the analysis. In some embodiments, the biopsied cells are flash frozen prior to the analysis.

In some embodiments, the disease tissue sample comprises a circulating metastatic cancer cell. In some embodiments, the disease tissue sample is obtained by sorting circulating tumor cells (CTCs) from blood. In a further embodiment, the CTCs have detached from a primary tumor and circulate in a bodily fluid. In yet a further embodiment, the CTCs have detached from a primary tumor and circulate in the bloodstream. In a further embodiment, the CTCs are an indication of metastasis. In some embodiments, the CTCs are pancreatic cancer cells. In some embodiments, the CTCs are colorectal cancer cells. In some embodiments, the CTCs are non-small cell lung carcinoma cells.

The variation can be identified based on the genomic sequence in the disease tissue in the individual. For example, genomic DNA can be obtained from the disease tissue in the individual and subjected to sequencing analysis. The sequence so obtained can then be compared to those obtained from a reference sample. In some embodiments, the disease sample is subjected to whole-genome sequencing. In some embodiments, the disease sample is subjected to whole-exome sequencing, i.e., only exons in the genomic sequences are sequenced. In some embodiments, the genomic sequences are "enriched" for specific sequences prior to the comparison to a reference sample. For example, specific probes can be designed to enrich certain desired sequences (for example disease-specific sequences) before being subjected to sequencing analysis. Methods of whole-genomic sequencing, whole-exome sequencing, and targeted sequencing are known in the art and reported, for example, in Bentley, D. R. et al., Accurate whole human genome sequencing using reversible terminator chemistry, *Nature,* 2008, v. 456, 53-59; Choi, M. et al., *Genetic diagnosis by whole exome capture and massively parallel DNA sequencing, Proceedings of the National Academy of Sciences,* 2009, v. 106(45), 19096-19101; and Ng, S. B. et al., Targeted capture and massively parallel sequencing of 12 human exomes, *Nature,* 2009, v. 461, 272-276, which are hereby incorporated by reference.

In some embodiments, the variations are identified based on the transcriptome sequences in the disease tissue in the individual. For example, whole or partial transcriptome sequences (for example by methods such as RNA-Seq) can be obtained from the disease tissue in the individual and subjected to sequencing analysis. The sequence so obtained can then be compared to those obtained from a reference sample. In some embodiments, the disease sample is subjected to whole-transcriptome RNA-Seq sequencing. In some embodiments, the transcriptome sequences are "enriched" for specific sequences prior to the comparison to a reference sample. For example, specific probes can be designed to enrich certain desired sequences (for example disease-specific sequences) before being subjected to sequencing analysis. Methods of whole-transcriptome sequencing and targeted sequencing are known in the art and reported, for example, in Tang, F. et al., mRNA-Seq whole-transcriptome analysis of a single cell, *Nature Methods,* 2009, v. 6, 377-382; Ozsolak, F., RNA sequencing: advances, challenges and opportunities, *Nature Reviews,* 2011, v. 12, 87-98; German, M. A et al., Global identification of microRNA-target RNA pairs by parallel analysis of RNA ends, *Nature Biotechnology,* 2008, v. 26, 941-946; and Wang, Z. et al., RNA-Seq: a revolutionary tool for transcriptomics, *Nature Reviews,* 2009, v. 10, p. 57-63. In some embodiments, transcriptomic sequencing techniques comprise, but are not limited to, RNA poly(A) libraries, microarray analysis, parallel sequencing, massively parallel sequencing, PCR, and RNA-Seq. RNA-Seq is a high-throughput technique for sequencing part of, or substantially all of, the transcriptome. In short, an isolated population of transcriptomic sequences is converted to a library of cDNA fragments with adaptors attached to one or both ends. With or without amplification, each cDNA molecule is then analyzed to obtain short stretches of sequence information, typically 30-400 base pairs. These fragments of sequence information are then aligned to a reference genome, reference transcripts, or assembled de novo to reveal the structure of transcripts (i.e., transcription boundaries) and/or the level of expression.

Once obtained, the sequences in the disease tissue can be compared to the corresponding sequences in a reference sample. The sequence comparison can be conducted at the nucleic acid level, by aligning the nucleic acid sequences in the disease tissue with the corresponding sequences in a reference sample. Sequence variations that lead to one or more changes in the encoded amino acids are then identified. Alternatively, the sequence comparison can be conducted at the amino acid level, that is, the nucleic acid sequences are first converted into amino acid sequences in silico before the comparison is carried out.

In some embodiments, comparison of a sequence from the disease tissue to those of a reference can be completed by techniques known in the art, such as manual alignment, FAST-All (FASTA), and Basic Local Alignment Search Tool (BLAST). Sequence comparison completed by BLAST requires input of a disease sequence and input of a reference sequence. BLAST compares a disease sequence to a reference database by first identifying short sequence matches between two sequences, a process referred to as seeding. Once a sequence match is found, expansion of the sequence alignment is performed using a scoring matrix.

In some embodiments, the reference sample is a matched, disease-free tissue sample. As used herein, a "matched," disease-free tissue sample is one that is selected from the same or similar tissue type as the disease tissue. In some embodiments, a matched, disease-free tissue and a disease tissue may originate from the same individual. The reference sample described herein in some embodiments is a disease-free sample from the same individual. In some embodiments, the reference sample is a disease-free sample from a different individual (for example an individual not having the disease). In some embodiments, the reference sample is obtained from a population of different individuals. In some embodiments, the reference sample is a database of known genes associated with an organism. In some embodiments, a reference sample may be a combination of known genes associated with an organism and genomic information from a matched disease-free tissue sample. In some embodiments, a variant-coding sequence may encode or comprise a point mutation in the amino acid sequence. In some embodiments, the variant-coding sequence may encode or comprise an amino acid deletion or insertion.

In some embodiments, the set of variant-coding sequences are first identified based on genomic sequences. This initial set is then further filtered to obtain a narrower set of expression variant-coding sequences based on the presence of the variant-coding sequences in a transcriptome sequencing database (and is thus deemed "expressed"). In some embodiments, the set of variant-coding sequences are reduced by at least about 10, 20, 30, 40, 50, or more times by filtering through a transcriptome sequencing database.

In some embodiments, the variant-coding sequence is a sequence that results from a non-synonymous mutation leading to a different amino acid(s) in the protein (e.g., point mutations). In some embodiments, the variant-coding sequence is a sequence that results from a read-through mutation in which a stop codon is modified or deleted, leading to translation of a longer protein with a novel tumor-specific sequence at the C-terminus. In some embodiments, the variant-coding sequence is a sequence that results from a splice site mutation that leads to the inclusion of an intron in the mature mRNA and thus a unique tumor-specific protein sequence. In some embodiments, the variant-coding sequence is a sequence that results from a chromosomal rearrangement that gives rise to a chimeric protein with tumor-specific sequences at the junction of 2 proteins (i.e., gene fusion). In some embodiments, the variant-coding sequence is a sequence that results from a frameshift mutation or deletion that leads to a new open reading frame with a novel tumor-specific protein sequence. In some embodiments, the variant-coding sequence is a sequence that results from more than one mutation. In some embodiments, the variant-coding sequence is a sequence that results from more than one mutation mechanism.

Obtaining Epitope Variant-Coding Sequences

The variant-coding sequences described herein in some embodiments are filtered to obtain a smaller set of variant-coding sequences encoding peptides that are predicted to bind an MHC molecule ("epitope variant-coding sequences"). In some embodiments, the set of variant-coding sequences are reduced by at least about 10, 20, 30, 40, 50, 60, 80, 100, 150, 200, 250, 300, or more times by filtering through the MHC binding prediction process.

The ability of the peptides encoded by the variant-coding sequence to bind to MHC (such as MHCI) may be assessed by a prediction algorithm, such as NETMHC. In short, NETMHC is an algorithm trained on quantitative peptide data using both affinity data from the Immune Epitope Database and Analysis Resource (IEDB) and elution data from SYFPEITHI. Predictions of MHCI binding may be made for peptides between 8 and 14 amino acids in length. NETMHC uses predictors trained on 9-mer amino acid sequences from 55 MHC alleles (43 human and 12 non-human). To allow for the prediction of shorter input sequences, NETMHC will virtually extend an 8-mer amino acid sequence. For input sequences longer than a 9-mer, NETMHC will generate all possible 9-mer amino acid sequences contained within the input sequence. NETMHC then uses trained artificial neural networks and position specific scoring matrices to predict MHC binding.

Selecting Immunogenic Variant-Coding Sequences

The methods provided herein in some embodiments further comprise selecting immunogenic variant-coding sequences comprising predicting immunogenicity of the peptides comprising a variant amino acid encoded by the variant-coding sequences. The prediction of immunogenicity can be carried out, for example, by a process (such as an in in silico process) which consider one or more parameters of the peptide and the corresponding peptide precursor to predict the likelihood that the peptide is immunogenic. These parameter include, but are not limited to, i) binding affinity of the peptide to the MHCI molecule; ii) protein level of a peptide precursor containing the peptide; iii) expression level of the transcript encoding the peptide precursor; iv) processing efficiency of the peptide precursor by an immunoproteasome; v) timing of the expression of the transcript encoding the peptide precursor; vi) binding affinity of the peptide to a TCR molecule; vii) position of a variant amino acid within the peptide; viii) solvent exposure of the peptide when bound to a MHCI molecule; ix) solvent exposure of the variant amino acid when bound to a MHCI molecule; x) content of aromatic residues in the peptide; and xi) nature of the peptide precursor. In some embodiments, the immunogenicity is based on at least 2, 3, 4, 5, 6, 7, 8, 9, or 10 of the parameters described herein.

In some embodiments, the binding affinity of the peptide to the MHC molecule is used for predicting immunogenicity. The binding affinity of peptide to an MHC molecule may be predictive of the stability of the pMHC, which in turn may allow for prolonged presentation of the pMHC, thus increasing cell surface exposure for potential interaction with immune cells. Binding affinity may be predicted using known techniques in the art, such as RankPep, MHCBench, nHLAPred, SVMHC, NETMHCpan, and POPI, which are based on methodology such as artificial neural networks, average relative binding matrices, quantitative matrices, and stabilized matrix methods. In some embodiments, the binding affinity of a peptide to MHC is based on the presence of specific amino acid residues located in known anchor positions (amino acids involved in MHC binding). In some embodiments, each residue in the peptide is evaluated for its contribution to binding. In some embodiments, analysis systems are trained with peptides known to bind MHC. In some embodiments, the binding energy of a peptide-MHC molecule is calculated. In some embodiments, a binding threshold is used to evaluate predicted affinity of peptides to bind to MHC, such as an IC50 value <500 nM.

In some embodiments, the expression level of the peptide precursor in the disease tissue is used for predicting immunogenicity. In some embodiments, the protein level is measured biochemically (such as Western blot and ELISA). In some embodiments, the protein level may be measured by known quantitative mass spectrometry techniques. As demonstrated by La Gruta et al., high expression levels of peptide precursors in disease tissue can be correlated with predicted immunogenicity. As described, the availability of larger quantities of peptide precursors that feed into epitope processing pathways has been positively correlated with increased epitope presentation and immunogenic response (La Gruta, N. L. et al., A virus-specific CD8+ T cell immunodominance hierarchy determined by antigen dose and precursor frequencies, *Proceedings of the National Academy of Sciences,* 2006, v. 103, 994-999, which is hereby incorporated by reference).

In some embodiments, the expression levels of the transcript encoding the peptide precursor in the disease tissue may be used for predicting immunogenicity. In some embodiments, the RNA expression level is measured by RT-PCR. In some embodiments, the RNA expression level is measured by sequencing analysis. As discussed above, increasing the availability of peptide precursors for epitope processing pathways positively correlates with the immunogenic response associated with said epitopes resulting from said peptide precursors. Further, a positive correlation between mRNA levels and protein abundance has been observed (Ghaemmaghami, S. et al., Global analysis of protein expression in yeast, *Nature,* 2003, v. 425, 737-741, which is hereby incorporated by reference). Therefore, expression levels of the transcript encoding the peptide precursor in the disease tissue may be used for predicting immunogenicity.

In some embodiments, the processing efficiency of the peptide precursor by an immunoproteasome is used for predicting immunogenicity. As used herein, the "processing efficiency" of a peptide precursor refers to the efficiency in which source amino acid sequences (i.e., larger peptides or proteins) are expressed, translated, transcribed, digested, transported, and any further processing prior to binding an MHCI molecule. An "immunoproteasome" is a collection of proteases that enzymatically digest the peptide and/or protein precursors into small amino acid sequences for the ultimate purpose of epitope formation. For example, as demonstrated by Chen et al., the ability of the immunoproteasome to generate epitope precursors directly correlates with immunogenicity (Chen, W. et al., Immunoproteasomes shape immunodominance hierarchies of antiviral CD8+ T cell repertoire and presentation of viral antigens, *The Journal of Experimental Medicine,* 2001, v. 193, 1319-1326, which is hereby incorporated by reference). Knowledge of steps involved in epitope processing may be used to predict immunogenicity of resulting epitopes. In particular, work on immunoproteasomes suggests it is efficient at producing MHC epitopes and the understanding of immunoproteasome mechanisms would facilitate prediction of immunogenic peptides.

In some embodiments, the timing of expression of the peptide precursor may be used for predicting immunogenicity. Proteins expressed earlier in disease progression are more likely to be presented as MHC epitopes (Moutaftsi, M. et al., A consensus epitope prediction approach identifies the breadth of murine T CD8+-cell responses to vaccina virus, *Nature Biotechnology,* 2006, v. 24, 817-819, which is hereby incorporated by reference). In some embodiments, comparative analyses of disease tissue may be used to determine the temporal expression pattern of gene products. In some embodiments, extrapolation of temporal expression patterns may allow for identification of expressed gene products that are presented in greater abundance at an early time point in comparison to other identified expressed gene products.

In some embodiments, the binding affinity of a peptide epitope with a T cell receptor (TCR) may be used for predicting immunogenicity. Methods of predicting the binding affinity of a peptide epitope with a TCR are known in the art and reported, for example, in Tung, C.-W. et al., POPISK: T-cell reactivity prediction using support vector machines and string kernels, *BMC Bioinformatics,* 2011, v. 12, 446, which is hereby incorporated by reference.

In some embodiments, the position of the variant amino acid in the peptide is used for predicting immunogenicity. A peptide epitope binds to a MHCI molecule at two distinct anchor positions. The span between anchor positions is separated by about 6-7 amino acid, as measured by the epitope peptide sequence, not inclusive of the amino acids occupying the anchor positions. It has been reported that mutations in the span of amino acids between the two MHCI anchor positions, namely amino acids in position 4-6, are more likely to positively correlate with an immunogenic response (Calis, J. J. A. et al., Properties of MHC class I presented peptides that enhance immunogenicity, *PLOS Computational Biology,* 2013, v. 9, 1-13, which is hereby incorporated by reference). The sequence position of an amino acid is determined by starting a sequence position count of 1 for a terminal amino acid.

In some embodiments, the structural characteristics of the peptide presented on the MHC presented epitope may be predictive of immunogenicity. Structural assessment of a MHC bound peptide may be conducted by in silico 3-dimensional analysis and/or protein docking programs. Methods of predicting the structure of a pMHC molecule are known in the art and reported, for example, in Marti-Renom, M. A. et al., Comparative protein structure modeling of genes and genomes, *Annual Review of Biophysics and Biomolecular Structure,* 2000, v. 29, 291-325, Chivian, D. et al., Homology modeling using parametric alignment ensemble generation with consensus and energy-based model selection, *Nucleic Acids Research,* 2006, v. 34, e112, and McRobb, F. M. et al., Homology modeling and docketing evaluation of aminergic G protein-coupled receptors, *Journal of Chemical Information and Modeling,* 2010, v. 50, 626-637, which are hereby incorporated by reference. Use of a predicted epitope structure when bound to a MHC molecule, such as acquired from the Rosetta algorithm, may be used to evaluate the degree of solvent exposure of an amino acid residues of said epitope when the epitope is bound to a MHC molecule. This information may be subsequently correlated with the immunogenicity of the peptide. For example, as described by Park et al., mutant peptides, wherein the variant amino acid residue displays additional solvent exposure as compared to the wild type sequence, are positively correlated with increased immunogenicity (Park, M.-S. et al., Accurate structure prediction of peptide-MHC complexes for identifying highly immunogenic antigens, *Molecular Immunology,* 2013, v. 56, 81-90, which is hereby incorporated by reference.) In some embodiments, the solvent exposure of the entire peptide when presented on the MHC complex is used for predicting immunogenicity. In some embodiments, the solvent exposure of the variant amino acid on the peptide is used for predicting immunogenicity.

In some embodiments, the epitope content of large and/or aromatic residues in the peptide may be used for predicting immunogenicity. Calis et al. observed a link between the presence of large and/or aromatic amino acid residue within the epitope amino acid sequence and immunogenicity. Specifically, it was reported that phenylalanine and isoleucine content was positively correlated with epitope immunogenicity. As discussed above, both location and structural assessment of variant-amino acids may be used to predict epitope immunogenicity. Further to this discussion, it was hypothesized that large and/or aromatic residues within position 4-6 of the epitope may be predicted to have a large degree of solvent exposure.

In some embodiments, the nature of the peptide precursor may be used to predict immunogenicity of a variant-coding amino acid sequence. For example, when the disease tissue is tumor, peptide precursor sequences that are known to be associated with cancer can be useful when predicting immunogenicity. However, peptide precursor sequences from proteins not directly associated with cancer, for example, when mutated, can also be useful within the methods of the present invention.

In some embodiments, at least two (such as at least any one 3, 4, 5, 6, 7, 8, 9, or 10) parameters described herein may be used to predict immunogenicity of a peptide. In some embodiments, a first predictive assessment may be used to select a set of variant-coding amino acid sequences that are subsequently processed by a second predictive assessment resulting in a cumulative prediction of epitope immunogenicity. It is intended as part of the instant disclosure that multiple rounds of assessment may be used to predict epitope immunogenicity. Alternatively, multiple parameters are assessed in parallel, and a composite score based on the assessment of various parameters can be obtained. For example, a score can be calculated for each of the parameters, and each parameter can be assigned a percentage weight. A composite scope can then be calculated based on the scores and percentage weight of each of the parameters assessed. A combination of sequential assessment coupled with in-parallel parameter assessment can also be used.

For a given variation in a variant-coding sequence, multiple overlapping putative mutant peptides of various lengths can be generated. In one embodiment, these multiple overlapping putative mutant peptides can be ranked based on immunogenicity which can encompass one or more analyses as described herein. Additionally, the ranking of putative mutant peptides can be accomplished by any one or multiple means well known in the art which can be included within the immunogenicity determination or be considered separate analyses depending on the preference of those conducting the ranking process. Some non-limiting examples of such means include abundance of the precursor protein, the abundance of the peptide within the processed proteome including the efficiency of this processing, and the abundance of the peptide within peptide-MHC complexes. Further examples of potential ranking analyses include but are not limited to binding affinity of the peptide, stability of the peptide-MHC complex, and the similarity or difference of the peptide from self-peptides. Alternatively, peptides can be ranked based on correlation with data produced from mass spectrometry methods measuring these or other characteristics well known to one or ordinary skill or described herein. Some representative characteristics include the presence or absence of large or aromatic amino acids, which increases immunogenicity and the particular positions that these amino acids are found within the peptide, with immunogenicity impact preference given to those amino acids found in the middle positions of the peptide, for example, peptides four through six (see, e.g., Calis et al. PLOS, 9(10):e1003266 (2013)).

In some embodiments, the prediction of immunogenicity further comprises HLA (human leukocyte antigen)-typing analysis. Because of the polygeny of the MHC, every person will express at least three different antigen-presenting MHC class I molecules and three (or sometimes four) MHC class II molecules on his or her cells. In fact, the number of different MHC molecules expressed on the cells of most people is greater because of the extreme polymorphism of the MHC and the codominant expression of MHC gene products. There are more than 200 alleles of some human MHC class I and class II genes, each allele being present at a relatively high frequency in the population. So there is only a small chance that the corresponding MHC locus on both the homologous chromosomes of an individual will have the same allele; most individuals will be heterozygous at MHC loci. The particular combination of MHC alleles found on a single chromosome is known as an MHC haplotype. Expression of MHC alleles is codominant, with the protein products of both the alleles at a locus being expressed in the cell, and both gene products being able to present antigens to T cells. The extensive polymorphism at each locus thus has the potential to double the number of different MHC molecules expressed in an individual and thereby increases the diversity already available through polygeny (see, e.g. Janeway's Immunobiology, Murphy, Kenneth, ed., Garland Science, New York, N.Y. (2011) for general overview). HLA-typing can be accomplished using any one of several methods known in the prior art, such as DNA based histocompatability assays. Particular examples of methods in the art involve polymerase chain reaction (PCR) product further analyzed such as PCR-RFLP (restriction fragment length polymorphism), PCR-SSO (sequence specific oligonucleotides), PCR-SSP (sequence specific primers), and PCR-SBT (sequence based typing) techniques. Thus determining the particular gene polymorphism type involved in the presentation of the peptide of interest can provide further information about the immunogenicity of the mutant peptides.

Obtaining Peptides Bound to MHC Molecules

The methods provided herein in some embodiment comprising obtaining peptides bound to MHC molecules from the disease tissue of an individual. In some embodiments, the MHC-bound peptides are isolated by immunoaffinity techniques. In some embodiments, the MHC-bound peptides are isolated by affinity chromatography. In some embodiments, the MHC-bound peptides are isolated by immunoaffinity affinity chromatography. In some embodiments, the MHC-bound peptides are isolated by immunoprecipitation techniques.

In some embodiments, an anti-MHC antibody is used to capture the MHC/peptide molecule. In some embodiments, multiple anti-MHC antibodies, optionally with differing affinities and/or binding characteristics, may be used to capture the MHC/peptide complexes. Suitable antibodies include, but are not limited to, monoclonal antibody W6/32, specific for HLA class I, and monoclonal antibody BB7.2, specific for HLA-A2.

In some embodiments, a MHC/peptide complex may be first isolated, and the MHC-bound peptides are subsequently separated from the MHC molecule. In some embodiments, a MHC-bound peptide is separated from a MHC molecule by acid elution. In some embodiments, acid-mediated separation of a MHC-bound peptide from a MHC molecule may be performed on intact whole cells, optionally in the presence of lysed cells and/or cell remnants. In some embodiments, a MHC-bound peptide may be separated from a MHC molecule following exposure of a pMHC to a buffer with an acidic pH. In some embodiments, a MHC-bound peptide may be separated from a MHC molecule by mild acid elution (MAE). In some embodiments, a MHC-bound peptide may be separated from a MHC molecule by mild acid elution (MAE) of an extracellular surface. In some embodiments, a MHC-bound peptide may be separated from a MCH molecule by denaturation of the pMHC molecule.

In some embodiments, the MHC-bound peptide may be further processed prior to mass spectrometry-based sequencing. In some embodiments, the MHC-bound peptide may be concentrated prior to mass spectrometry-based sequencing. In some embodiments, the MHC-bound peptide may be purified prior to mass spectrometry-based sequencing. In some embodiments, the MHC-bound peptide may be fractionated prior to mass spectrometry-based sequencing. In some embodiments, the MHC-bound peptide may be enriched prior to mass spectrometry-based sequencing. In some embodiments, the MHC-bound peptide may be further enzymatically digested prior to mass spectrometry-based sequencing. In some embodiments, a buffer, in which the MHC-bound peptide may be contained, may be exchanged prior to mass spectrometry-based sequencing. In some embodiments, the MHC-bound peptide may be labeled prior to mass spectrometry-based sequencing. In some embodiments, the MHC-bound peptide may be covalently labeled prior to mass spectrometry-based sequencing. In some embodiments, the MHC-bound peptide may be enzymatically labeled prior to mass spectrometry-based sequencing. In some embodiments, the MHC-bound peptide may be chemically labeled prior to mass spectrometry-based sequencing. In some embodiments, the MHC-bound peptide may be labeled to allow for enhanced ionization during mass spectrometry-based sequencing. In some embodiments, the MHC-bound peptide may be labeled to allow for quantification during mass spectrometry-based sequencing. In some embodiments, isolated MHC-bound peptides may originate from multiple sources and/or enrichment procedures and optionally may be collectively pooled prior to mass spectrometry-based sequencing.

Mass Spectrometry-Based Peptide Sequencing

The peptides bound to MHC molecules in the methods described herein are subjected to mass spectrometry sequencing. As used herein, "mass spectrometry-based sequencing" refers to the technique of identifying an amino acid sequence of a peptide and/or protein by use of mass spectrometry. A mass spectrometer is an instrument capable of measuring the mass-to-charge (m/z) ratio of individual ionized molecules, allowing researchers to identify unknown compounds, to quantify known compounds, and to elucidate the structure and chemical properties of molecules. The methods provided herein may be used to obtain sequence information of a peptide epitope bound to a MHCI molecule. In some embodiments, the entire sequence of a peptide epitope may be determined. In some embodiments, a partial sequence of the peptide epitope may be determined. In some embodiments, the peptides are subjected to tandem mass spectrometry such as tandem chromatography mass spectrometry (for example LC-MS or LC-MS-MS).

In some embodiments, one begins mass spectrometry analysis by isolating and loading a sample onto the instrument. In some embodiments, the MHC-bound peptide may be chromatographically processed prior to mass spectrometry analysis. In some embodiments, chromatography is liquid chromatography. In some embodiments, chromatography is reverse phase chromatography. In some embodiments, the MHC-bound peptide may be chromatographically separated, and simultaneously concentrated, prior to introduction into the mass spectrometer. In some embodiments, chromatographic separation may be online, wherein peptides eluting from the chromatography source enter directly into mass spectrometer. In some embodiments, chromatographic separation may be offline. In some embodiments, offline chromatographic separation may be used to fractionate isolate MHC-bound peptides. Offline chromatographic separation typically involves separation and/or fractionation of a mass spectrometry sample wherein the resulting separated and/or fractionated sample is not immediate introduced into the mass spectrometer as the sample exits the chromatographic system.

In some embodiments, the MHC-bound peptide may be sequenced using known mass spectrometry ionization techniques (such as matrix-assisted laser desorption/ionization, electrospray ionization, and/or nano-electrospray ionization, atmospheric pressure chemical ionization). In some embodiments, the MHC-bound peptide may be ionized outside, inside, and/or as they enter the mass spectrometer. In some embodiments, a positive ion of the MHC-bound peptide may be analyzed in the mass spectrometer. Subsequently, the ions are separated according to their mass-to-charge ratio via exposure to a magnetic field. In some embodiments, a sector instrument is used, and the ions are quantified according to the magnitude of the deflection of the ion's trajectory as it passes through the instrument's electromagnetic field, which is directly correlated to the ions mass-to-charge ratio. In other embodiments, ion mass-to-charge ratios are measured as the ions pass through quadrupoles, or based on their motion in three dimensional or linear ion traps or Orbitrap, or in the magnetic field of a Fourier transform ion cyclotron resonance mass spectrometer. The instrument records the relative abundance of each ion, which is used to determine the chemical, molecular and/or isotopic composition of the original sample. In some embodiments, a time-of-flight instrument is used, and an electric field is utilized to accelerate ions through the same potential, and measures the time it takes each ion to reach the detector. This approach depends on the charge of each ion being uniform so that the kinetic energy of each ion will be identical. The only variable influencing velocity in this scenario is mass, with lighter ions traveling at larger velocities and reaching the detector faster consequently. The resultant data is represented in a mass spectrum or a histogram, intensity vs. mass-to-charge ratio, with peaks representing ionized compounds or fragments.

Mass spectra data can be obtained by tandem mass spectrometry. In some embodiments, a mass spectrometry acquisition technique for acquiring information for peptide sequencing of the MHC-bound peptide may be data-dependent. In some embodiments, a mass spectrometry acquisition technique for acquiring information for peptide sequencing of the MHC-bound peptide may be data-independent. In some embodiments, a mass spectrometry acquisition technique for acquiring information for peptide sequencing of the MHC-bound peptide may be based on measured accurate mass mass spectrometry. In some embodiments, a mass spectrometry acquisition technique for acquiring information for peptide sequencing of the MHC-bound peptide may be peptide mass fingerprinting. Mass spectra data useful in this invention can be obtained by peptide mass fingerprinting. Peptide mass fingerprinting involves inputting the observed mass from a spectrum of the mixture of peptides generated by proteolytic digestion into a database and correlating the observed masses with the predicted masses of fragments arising from digestions of known proteins in silico. Known masses corresponding to sample masses provide evidence that the known protein is present in the sample tested.

In some embodiments, tandem mass spectrometry includes a process that causes peptide ions to collide with gas and to fragment (e.g., due to vibrational energy imparted by the collision). The fragmentation process produces cleavage products that break at the peptide bonds at various sites along the protein. The observed fragments' masses may be matched with a database of predicted masses for one of many given peptide sequences, and the presence of a protein may be predicted. In some embodiments, a mass spectrometry acquisition technique may utilize fragmentation techniques (such as collision-induced dissociation, pulsed-Q dissociation, higher-energy collisional dissociation, electron-transfer dissociation, and electron-transfer dissociation, infrared multiphoton dissociation).

In some embodiments, data acquired from the mass spectrometer may be used to identify a peptide sequence. In some embodiments, a search algorithm (such as SEQUEST and Mascot) may be used to assign a peptide sequence to an acquired mass spectrum. In some embodiments, assigned peptide sequences may have a false discovery rate of less than about 5%. In some embodiments, the assigned peptide sequences may have a false discovery rate of less than about 1%. In some embodiments, the assigned peptide sequences may have a false discovery rate of less than about 0.5%. In some embodiments, a database may be used by a search algorithm to make peptide sequence assignments of an acquired spectrum. In some embodiments, a database used by a search algorithm to make a peptide sequence assignment of an acquired spectrum may be a database of known sequences of an organism. In some embodiments, a database used by a search algorithm to make a peptide sequence assignment of an acquired spectrum may be a database of known proteins of an organism. In some embodiments, a database used by a search algorithm to make a peptide sequence assignment of an acquired spectrum may be a database of known genomic sequences of an organism. In some embodiments, a database used by a search algorithm to make a peptide sequence assignment of an acquired spectrum may comprise sequence information obtained from a disease tissue. In some embodiments, a database used by a search algorithm to make a peptide sequence assignment of an acquired spectrum may comprise sequence information obtained from a disease-free tissue.

In some embodiments, a sequence assigned spectrum may be manually validated to confirm correct fragment ion assignments by the algorithm. In some embodiments, a synthetic peptide standard may be used to confirm an algorithm-assigned sequence. In some embodiments, a spectrum generated from the MHC-bound peptide may be compared to a spectrum generated from a peptide standard. For example, comparison may involve matching the pattern of fragment ions, and optionally fragment abundance or intensity, based on m/z values of the spectrum acquired from a disease tissue source to that of a reference. In some embodiments, manual validation may confirm a sequence assignment of the complete peptide sequence. In some embodiments, manual validation may confirm the sequence assignment of a partial segment of a peptide sequence.

Correlation of Mass Spectrometry and Genomic Data

The methods provided herein in some embodiments comprise correlating the mass spectrometry-derived sequence information of the MHC-bound peptides with a set of variant-coding sequences to identify disease-specific immunogenic mutant peptides. For example, the mass spectrometry sequence of a MHC-bound peptide may be used to further select a population of predicted disease-specific immunogenic mutant peptides. In some embodiments, mass spectrometry-based epitope identification may supplement genomic-based immunogenic epitope identification and/or prediction. In some embodiments, mass spectrometry-based epitope identification may confirm genomic-based immunogenic epitope identification and/or prediction.

The data obtained from a mass spectrometry analysis may be correlated with immunogenic peptides predictions based on genomic and/or transcriptomic sequence analysis of a disease tissue. In general, the amino acid sequence identified from mass spectrometry-based sequencing is compared with amino acid sequences of predicted immunogenic peptides to find regions comprising partial sequence alignment. In some embodiments, the peptide identified via mass spectrometry will be an exact sequence match to the sequence of the predicted immunogenic peptide. In some embodiments, the length of the amino acid sequence may vary between the peptide identified via mass spectrometry and that of the predicted immunogenic peptide. For example, a peptide identified via mass spectrometry may contain additional amino acids amended to the C- and/or N-terminus of the peptide as compared to the predicted immunogenic peptide. Alternatively, a peptide identified via mass spectrometry comprising a variant amino acid may have fewer amino acids on the C- and/or N-terminus as compared to the predicted immunogenic peptide. In these exemplary embodiments, the variant amino acid and the sequence surrounding the variant amino acid must be the same in both the peptide identified via mass spectrometry and the peptide predicted to be immunogenic. In some embodiments, the result obtained from correlating mass spectrometry-based sequences with immunogenic peptide predictions is to match predicted immunogenic sequences with sequences that are confirmed, via mass spectrometry-based sequencing, to be physically presented by MHC molecules.

In some embodiments, the acquired mass spectrometry sequence identifications may be further filtered by peptide length. For example, in some embodiments, the population of MHC-bound peptides identified by mass spectrometry may be further filter to include only those identified peptide sequences that are 8 or 9 amino acids in length.

Functional Validation of Immunogenic Mutant Peptides

The disease-specific, immunogenic mutant peptides identified by the methods described herein can further be validated by functional studies. For example, the peptide may be synthesized and tested based on the ability to activate a targeted immune response (such as that mediated by cytotoxic T cells). In some embodiments, the peptide is synthesized chemically. In some embodiments, a peptide is synthesized by recombinant methods. In some embodiments, a peptide is synthesized by first expressing a peptide precursor molecule which is then processed (for example by an immunoproteasome) to produce the peptide of interest. The synthesized peptides can be subjected to further purification before being subjected to functional analysis.

In some embodiments, a synthetic predicted disease-specific immunogenic peptide is used in vitro to test for cytotoxic T cell response. In some embodiments, a synthetic predicted disease-specific immunogenic peptide is used in vivo to test for cytotoxic T cell response.

In some embodiments, immunogenicity of a disease-specific peptide may be tested by immunization of a mouse. In some embodiments, immunogenicity of a disease-specific peptide may be tested following immunization by measuring CD8 T cell response. In some embodiments, a CD8 T cell response may be measured using MHCI/peptide-specific dextramers. In some embodiments, immunogenicity of a disease-specific peptide may be tested by analyzing tumor-infiltrating cells (TILs).

In some embodiments, the presence of specific epitopes and/or cell surface proteins may be measured. In some embodiments, the presence of epitopes originating from the vaccination may be measured. In some embodiments, interferon gamma (IFN-γ) may be measured. In some embodiments, programmed cell death 1 (PD-1) may be measured. In some embodiments, T cell immunoglobulin mucin-3 (TIM-3) may be measured. In some embodiments, cytotoxic T cells expressing specific proteins and/or epitopes may be measured. In some embodiments, cytotoxic T cells displaying specific epitopes may be measured.

In some embodiments, the immunogenicity of a disease-specific peptide may be tested by first expressing the peptide in a dendritic cell and then testing for the ability of the presented antigen to be recognized by a T cell. In some embodiments, the dendritic cell is obtained from a patient, wherein the disease-specific peptide was identified in said patient. In some embodiments, the immunogenicity of a disease-specific peptide may be tested by first expressing the peptide in a B-lymphocyte and then testing for the ability of the presented antigen to be recognized by a T cell. In some embodiments, the B-lymphocyte is obtained from a patient, wherein the disease-specific peptide was identified in said patient. See, e.g., U.S. Pat. No. 8,349,558.

Compositions of Immunogenic Peptides

The present disclosure provides methods of identifying a disease-specific immunogenic peptide. An immunogenic peptide may be identified based on the ability to activate a targeted immune response (such as that mediated by cytotoxic T cells). In some embodiments, the amino acid sequence of an identified disease-specific immunogenic peptide may be used develop a pharmaceutically acceptable composition. In some embodiments, a composition may comprise a synthetic disease-specific immunogenic peptide. In some embodiments, a composition may comprise a synthetic disease-specific immunogenic mutant peptide. In some embodiments, a composition may comprise two or more disease-specific immunogenic peptides. In some embodiments, a composition may comprise two or more disease-specific immunogenic mutant peptides. In some embodiments, the two or more disease-specific immunogenic peptides may activate a cytotoxic T cell response to two or more unique epitopes.

In some embodiments, a composition may comprise a precursor to a disease-specific immunogenic peptide (such as a protein, peptide, DNA and RNA). In some embodiments, a precursor to a disease-specific immunogenic peptide may generate or be generated to the identified disease-specific immunogenic peptide. In some embodiments, the precursor to a disease-specific immunogenic peptide may be a pro-drug.

In some embodiments, the composition comprising a disease-specific immunogenic peptide may be pharmaceutically acceptable. In some embodiments, the composition comprising a disease specific immunogenic peptide may further comprise an adjuvant. For example, the mutated peptide can be utilized as a vaccine (see, Sahin et al., Int. J. Cancer, 78:387-9 (1998); Stumiolo et al., Nature Biotechnol, 17:555-61 (1999); Rammensee et al., Immunol Rev 188: 164-76 (2002); and Hannani et al. Cancer J 17:351-358 (2011)). Furthermore, the vaccine may contain individualized components, according to the personal needs of the particular patient. In some embodiments, the vaccine may be specific to an immunogenic peptide predicted in a particular patient. In some embodiments, the vaccine will contain more than one immunogenic peptide or peptide precursor. In some embodiments, the length of the peptide used in the vaccine may vary in length. In some embodiments, the peptide is about 7 to 50 amino acids in length (such as about any of 8, 9, 10, 11, 12, 13, 14, 15, 17, 20, 22, 25, 30, 35, 40, 45, or 50 amino acids in length). In some embodiments, the peptide is about 8 to 12 amino acids in length. In some embodiments, the peptide is about 8 to 10 amino acids in length. The peptide can be utilized in its isolated form, or alternatively, peptides can be added to the ends of the MHC isolated peptide to produce a "long peptide" that may prove more immunogenic (see, e.g. Castle et al., Cancer Res 72:1081-1091 (2012)). In some embodiments, the peptide may also be tagged, or be a fusion protein, or be hybrid molecule. In some embodiments, the peptide is in the form of a pharmaceutically acceptable salt.

In some embodiments, the vaccine is a nucleic acid vaccine. In some embodiments, the nucleic acid encodes an immunogenic peptide or peptide precursor. In some embodiments, the nucleic acid vaccine comprises sequences flanking the sequence coding the immunogenic peptide or peptide precursor. In some embodiments, the nucleic acid vaccine comprises more than one immunogenic epitope. In some embodiments, the nucleic acid vaccine is a DNA-based vaccine. In some embodiments, the nucleic acid vaccine is a RNA-based vaccine. In some embodiments, the RNA-based vaccine comprises mRNA. In some embodiments, the RNA-based vaccine comprises naked mRNA. In some embodiments, the RNA-based vaccine comprises modified mRNA (e.g., mRNA protected from degradation using protamine. mRNA containing modified 5'CAP structure, or mRNA containing modified nucleotides). In some embodiments, the RNA-based vaccine comprises single-stranded mRNA.

The polynucleotide may be substantially pure, or contained in a suitable vector or delivery system. Suitable vectors and delivery systems include viral, such as systems based on adenovirus, vaccinia virus, retroviruses, herpes virus, adeno-associated virus or hybrids containing elements of more than one virus. Non-viral delivery systems include cationic lipids and cationic polymers (e.g., cationic liposomes). In some embodiments, physical delivery, such as with a 'gene-gun' may be used.

In some embodiments, the peptides described herein can be used for making mutant peptide specific therapeutics such as antibody therapeutics. For example, the mutant peptides can be used to raise and/or identify antibodies specifically recognizing the mutant peptides. These antibodies can be used as therapeutics. Synthetic short peptides have been used to generate protein-reactive antibodies. The advantage of immunizing with synthetic peptides is that unlimited quantity of pure stable antigen can be used. This approach involves synthesizing the short peptide sequences, coupling them to a large carrier molecule, and immunizing the animal of choice with the peptide-carrier molecule. The properties of antibodies are dependent on the primary sequence information. A good response to the desired peptide usually can be generated with careful selection of the sequence and coupling method. Most peptides can elicit a good response. The advantage of anti-peptide antibodies is that they can be prepared immediately after determining the amino acid sequence of a mutant peptide and the particular regions of a protein can be targeted specifically for antibody production.

Since the mutant peptides have been screened for high immunogenicity there is a high chance that the resulting antibody will recognize the native protein in the tumor setting. As in the vaccine situation, the length of peptide is another important factor to consider. Approximately, a peptide of 10-15 residues is optimal for anti-peptide antibody production; longer peptides are better since the number of possible epitopes increases with peptide length. However, long peptides increase the difficulties in synthesis, purification, and coupling to carrier proteins. The quality of an antibody is dependent upon the quality of the peptide. Side products contained in peptide products can lead to low-quality antibodies.

Peptide-carrier protein coupling is another factor involved in the production of high titer antibodies. Most coupling methods rely on the reactive functional groups in amino acids, such as —NH2, —COOH, —SH, and phenolic —OH. Site-directed coupling is the method of choice. Any suitable method used in anti-peptide antibody production can be utilized with the peptides identified by the methods of the present invention. Two such known methods are the Multiple Antigenic Peptide system (MAPs) and the Lipid Core Peptides (LCP method). The advantage of MAPs is that the conjugation method is not necessary. No carrier protein or linkage bond is introduced into the immunized host. One disadvantage is that the purity of the peptide is more difficult to control. In addition, MAPs can bypass the immune response system in some hosts. The LCP method is known to provide higher titers than other anti-peptide vaccine systems and thus can be advantageous.

Also provided herein are isolated MHC/peptide complexes comprising the disease specific immunogenic mutant peptides disclosed herein. Such MHC/peptide complexes can be used, for example, for identifying antibodies, soluble TCRs, or TCR analogs. One type of these antibodies has been termed TCR mimics as they are antibodies that bind peptides from tumor associated antigens in the context of specific HLA environments. This type of antibody has been shown to mediate the lysis of cells expressing the complex on their surface as well as protect mice from implanted cancer cells lines that express the complex (see, e.g., Wittman et al., J. of Immunol. 177:4187-4195 (2006)). One advantage of TCR mimics as IgG mAbs is that affinity maturation can be performed and the molecules are coupled with immune effector functions through the present Fc domain. These antibodies can also be used to target therapeutic molecules to tumors, such as toxins, cytokines, or drug products. Other types of molecules that have been developed using peptides such as those selected using the methods of the present invention using non-hybridoma based antibody production or production of binding competent antibody fragments such as anti-peptide Fab molecules on bacteriophage. These fragments can also be conjugated to other therapeutic molecules for tumor delivery such as anti-peptide MHC Fab-immunotoxin conjugates, anti-peptide MHC Fab-cytokine conjugates and anti-peptide MHC Fab-drug conjugates.

Methods of Treatment Comprising Immunogenic Vaccines

The present disclosure provides methods of treatment comprising an immunogenic vaccine. In some embodiments, a method of treatment for disease (such as cancer) is provided, which may comprise administering to an individual an effective amount of a composition comprising an immunogenic peptide. In some embodiments, a method of treatment for a disease (such as cancer) is provided, which may include administering to an individual an effective amount of a composition comprising a precursor of an immunogenic peptide. In some embodiments, an immunogenic vaccine may comprise a pharmaceutically acceptable disease-specific immunogenic peptide. In some embodiments, an immunogenic vaccine may comprise a pharmaceutically acceptable precursor to a disease-specific immunogenic peptide (such as a protein, peptide, DNA and RNA). In some embodiments, a method of treatment for a disease (such as cancer) is provided, which may include administering to an individual an effective amount of an antibody specifically recognizing the disease-specific, immunogenic mutant peptide. In some embodiments, a method of treatment for a disease (such as cancer) is provided, which may include administering to an individual an effective amount of a soluble TCR or TCR analog specifically recognizing the disease-specific, immunogenic mutant peptide.

In some embodiments, the cancer is any one of: carcinoma, lymphoma, blastema, sarcoma, leukemia, squamous cell cancer, lung cancer (including small cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, melanoma, endometrial or uterine carcinoma, salivary gland carcinoma, kidney or renal cancer, liver cancer, prostate cancer, vulval cancer, thyroid cancer, hepatic carcinoma, head and neck cancer, colorectal cancer, rectal cancer, soft-tissue sarcoma, Kaposi's sarcoma, B-cell lymphoma (including low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, and Waldenstrom's macroglobulinemia), chronic lymphocytic leukemia (CLL), acute lymphoblastic leukemia (ALL), myeloma, Hairy cell leukemia, chronic myeloblasts leukemia, and post-transplant lymphoproliferative disorder (PTLD), as well as abnormal vascular proliferation associated with phakomatoses, edema (such as that associated with brain tumors), and Meigs' syndrome.

The methods described herein are particularly useful in the personalized medicine context, where disease-specific, immunogenic mutant peptides obtained by any one of the methods described herein are used to develop therapeutics (such as vaccines or therapeutic antibodies) for the same individual. Thus, for example, in some embodiments, there is provided a method of treating a disease (such as cancer) in an individual, comprising: a) identifying a disease-specific, immunogenic mutant peptides in the individual; and b) synthesizing the peptide or peptide precursor; and c) administering the peptide to the individual. In some embodiments, there is provided a method of treating a disease (such as cancer) in an individual, comprising: 1) identifying a disease-specific, immunogenic mutant peptide in the individual; b) producing an antibody specifically recognizing the mutant peptide; and c) administering the peptide to the individual. In some embodiments, the identification step combines sequence-specific variant identification method with methods of immunogenicity prediction. In some embodiments, the identification step combines sequence-specific variant identification method with mass spectrometry. Any methods of identifying a disease-specific, immunogenic mutant peptide described herein can be used for the treatment methods described herein. In some embodiments, the method further comprises obtaining a sample of the disease tissue from the individual.

The methods provided herein can be used to treat an individual (e.g., human) who has been diagnosed with or is suspected of having cancer. In some embodiments, an individual may be a human. In some embodiments, an individual may be at least about any of 35, 40, 45, 50, 55, 60, 65, 70, 75, 80, or 85 years old. In some embodiments, an individual may be a male. In some embodiments, an individual may be a female. In some embodiments, an individual may have refused surgery. In some embodiments, an individual may be medically inoperable. In some embodiments, an individual may be at a clinical stage of Ta, Tis, T1, T2, T3a, T3b, or T4. In some embodiments, a cancer may be recurrent. In some embodiments, an individual may be a human who exhibits one or more symptoms associated with cancer. In some of embodiments, an individual may be genetically or otherwise predisposed (e.g., having a risk factor) to developing cancer.

The methods provided herein may be practiced in an adjuvant setting. In some embodiments, the method is practiced in a neoadjuvant setting, i.e., the method may be carried out before the primary/definitive therapy. In some embodiments, the method is used to treat an individual who has previously been treated. Any of the methods of treatment provided herein may be used to treat an individual who has not previously been treated. In some embodiments, the method is used as a first line therapy. In some embodiments, the method is used as a second line therapy.

In some embodiments, there is provided a method of reducing incidence or burden of preexisting cancer tumor metastasis (such as pulmonary metastasis or metastasis to the lymph node) in an individual, comprising administering to the individual an effective amount of a composition comprising an immunogenic vaccine.

In some embodiments, there is provided a method of prolonging time to disease progression of cancer in an individual, comprising administering to the individual an effective amount of a composition comprising an immunogenic vaccine.

In some embodiments, there is provided a method of prolonging survival of an individual having cancer, comprising administering to the individual an effective amount of a composition comprising an immunogenic vaccine.

In some embodiments, at least one or more chemotherapeutic agents may be administered in addition to the composition comprising an immunogenic vaccine. In some embodiments, the one or more chemotherapeutic agents may (but not necessarily) belong to different classes of chemotherapeutic agents.

In some embodiments, there is provided a method of treating a disease (such as cancer) in an individual, comprising administering: a) an immunogenic vaccine, and b) an immunomodulator. In some embodiments, there is provided a method of treating a disease (such as cancer) in an individual, comprising administering: a) an immunogenic vaccine, and b) an antagonist of a checkpoint protein. In some embodiments, there is provided a method of treating a disease (such as cancer) in an individual, comprising administering: a) an immunogenic vaccine, and b) an antagonist of programmed cell death 1 (PD-1), such as anti-PD-1. In some embodiments, there is provided a method of treating a disease (such as cancer) in an individual, comprising administering: a) an immunogenic vaccine, and b) an antagonist of programmed death-ligand 1 (PD-L1), such as anti-PD-L1. In some embodiments, there is provided a method of treating a disease (such as cancer) in an individual, comprising administering: a) an immunogenic vaccine, and b) an antagonist of cytotoxic T-lymphocyte-associated protein 4 (CTLA-4), such as anti-CTLA-4.

Example 1

This example demonstrates an exemplary methodology for prediction of immunogenic peptide epitopes.

Whole-exome sequencing was performed on MC-38 and TRAMP-C1 mouse tumor cell lines to identify tumor-specific point mutations. Coding variants were called relative to the reference mouse genome to identify 4285 and 949 non-synonymous variants in MC-38 and TRAMP-C1, respectively. Subsequently, the data were filtered for gene expression by RNA-Seq analysis and revealed that 1290 and 67 mutated genes were expressed in MC-38 and TRAMP-C1, respectively. 170 predicted neoepitopes in MC-38 and 6 predicted neoepitopes in TRAMP-C1 tumors were identified using the NETMHC-3.4 algorithm.

Figure 2A:
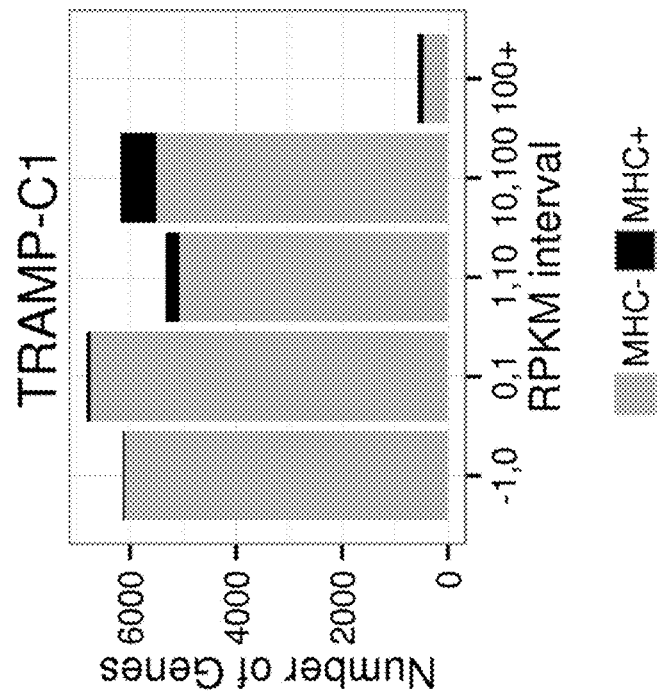
FIG. 2A illustrates the distribution of identified genes that were identified as epitopes presented on MHC molecules of the MC-38 cell line in relation to the measured reads per kilobase of exon model per million mapped reads (RPKM).
Figure 2B:
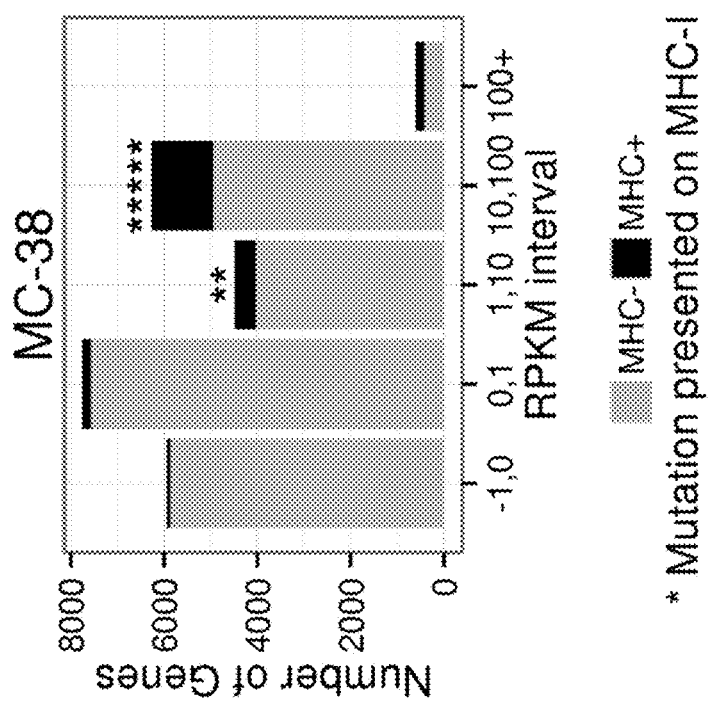
FIG. 2B illustrates the distribution of identified genes that were identified as epitopes presented on MHC molecules of the TRAMP-C1 cell line in relation to the measured RPKM.

Next, mass spectrometric analysis using a transcriptome-generated FASTA database revealed 797 unique H-2Kb epitopes and 725 unique H-2Db epitopes presented by the MC-38 cell line, and 477 unique H-2Kb epitopes and 332 unique H-2Db epitopes presented by the TRAMP-C1 cell line. It was observed that peptides derived from abundant transcripts are more likely to be presented by MHCI in MC-38 (FIG. 2A) and TRAMP-C1 (FIG. 2B) cells.

Of the 1290 and 67 amino-acid changes in MC-38 and TRAMP-C1, respectively, only 7 (7 in MC-38 and 0 in TRAMP-C1) were found to be presented on MHCI by mass spectrometry (Table 1). One epitope derived from the cancer testis self-antigen MAGE-D1 was also detected by mass spectrometry in MC-38 cells. These peptides were manually validated and compared to a synthetically generated version of the peptide for accuracy. All but one of these neoepitopes were predicted to bind MHCI (1050<500 nm, Table). Both wild type (WT) and mutant transcripts were expressed by the tumor cells and although most of the corresponding WT peptides were also predicted to bind MHCI, only three of them were detected by mass spectrometry.

Figure 3:
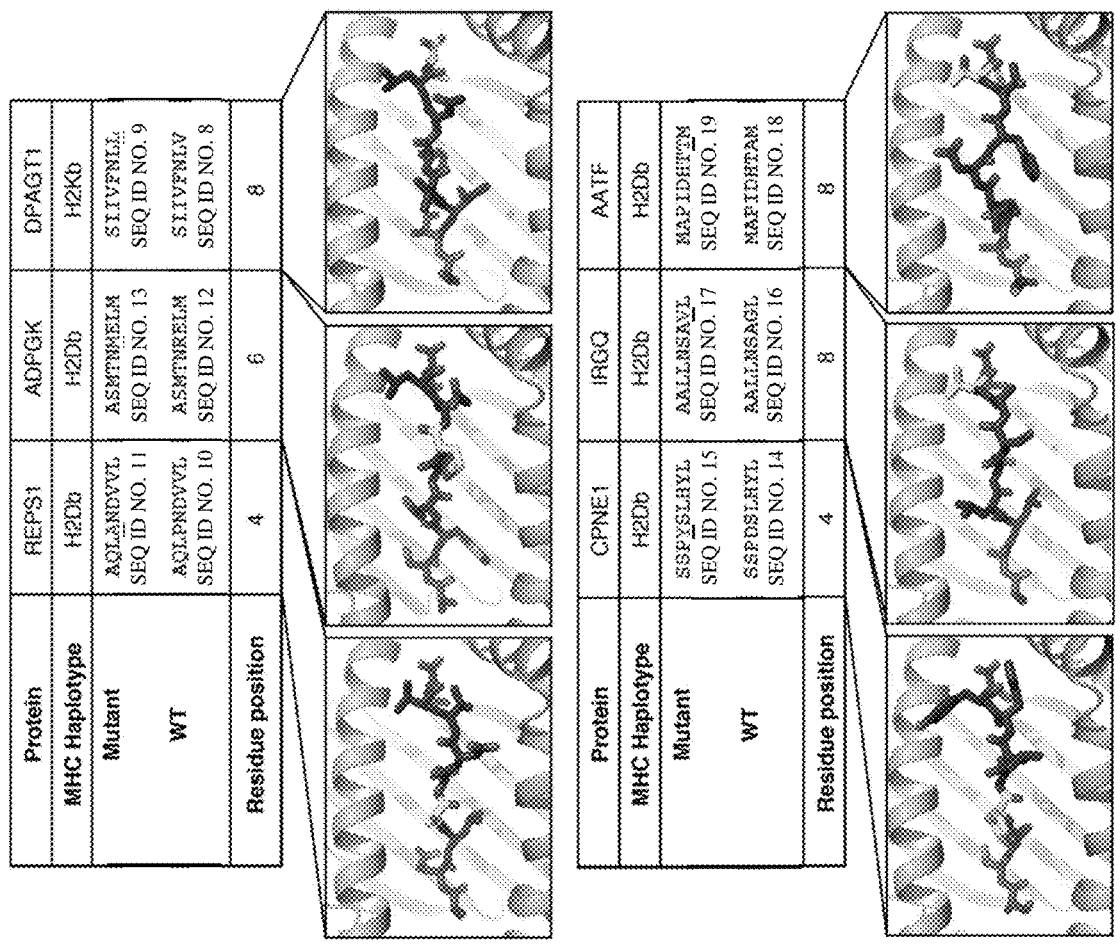
FIG. 3 illustrates structure modeling of peptides bound to MHC molecules.

Although there is a correlation between peptide binding affinity for MHCI and immunogenicity, other factors also contribute. For example, interaction of the mutated amino acid with the TCR is likely to be essential for the recognition of the mutated peptide as "non-self". This is especially true when the corresponding WT peptide is also presented on MHCI. Five out of the seven neoepitopes exhibited high binding prediction scores (IC50<50 nM by NETMHC3.4, Table 1). The other neoepitopes exhibited lower binding prediction scores suggesting that they might be less immunogenic. Utilizing published crystal structures of H-2Db and H-2Kb and a Rosetta-based algorithm to model each of the mutant peptides in complex with MHCI and analyze the potential for the mutant residue in each neoepitope to interact with the T cell receptor. In general, TCR recognition of displayed peptides is mediated by interactions with peptide residues 3 through 7. Among the peptides with high binding scores only in the Reps1 and Adpgk peptides have mutations within this range. Structure modeling also predicted that the mutated residues were oriented towards the solvent interface, and were thus judged to have good potential to be immunogenic (Table 1 and FIG. 3). On the other hand, the mutations in the Irgq, Aatf, Dpagt1 neoepitopes were found near the C-terminal end of the peptide, which likely falls outside of the TCR binding region and suggests that these neoepitopes were unlikely to be immunogenic (Table 1 and FIG. 3).

Figure 4A:
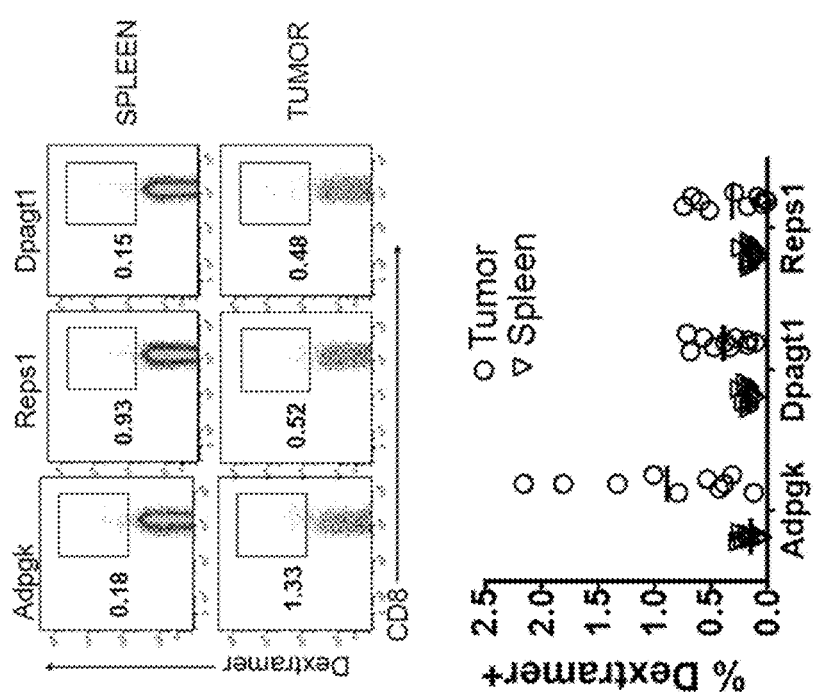
FIG. 4A illustrates percentage of peptide-specific CD8 T cells in wild type C57BL/6 mice immunized with select peptides.

Next, the immunogenicity of mutated tumor antigens evaluated by immunizing wild type C57BL/6 mice with long peptides encoding the mutated epitopes in combination with adjuvant and measured CD8 T cell responses using MHCI/peptide-specific dextramers. As shown in FIG. 4A, compared to the adjuvant alone group, three out of six peptides elicited a CD8 T-cell response. It was predicted that Reps1 and Adpgk to be immunogenic based on structure and binding affinity prediction and both elicited strong CD8 T cell responses. Of the four peptides predicted non-immunogenic, only Dpagt1 induced a weak CD8 T cells response.

Figure 4B:
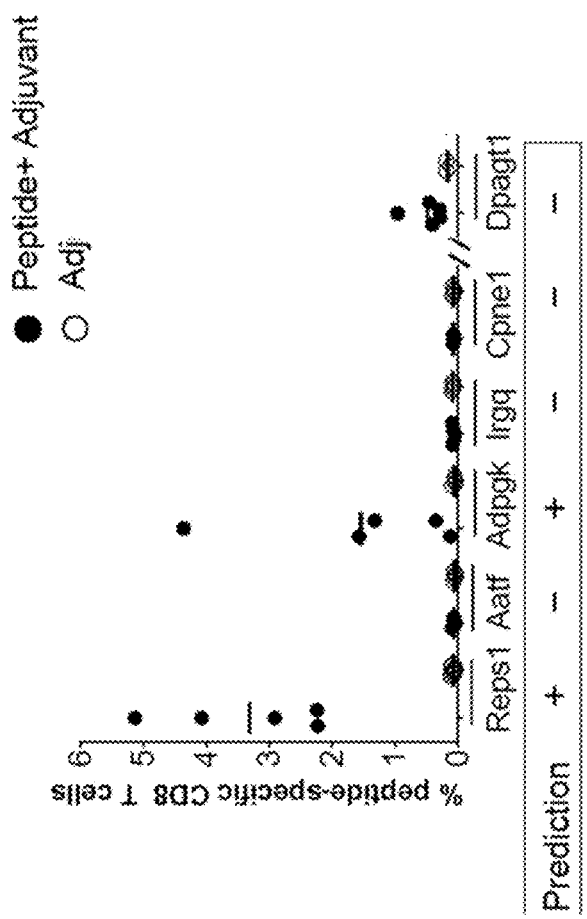
FIG. 4B illustrates percentage of dextramer positive CD8 T cells in the spleen and tumor.

The immunogenicity of these mutated peptides was confirmed in the context of the tumor by analyzing tumor-infiltrating cells (TILs). T cells specific for Reps1, Adpgk, and Dpagt1 were observed to be enriched in the tumor bed (FIG. 4B). Although there was heterogeneity, Adpgk-specific CD8 T cells were most abundant of the three and this was specific to MC-38 tumors as no Adpgk-specific CD8 T cells were detected in a syngeneic TRAMP-C1 tumors. Interestingly, the peptide derived from the single cancer testis self-antigen (MAGE-D1) identified by mass spectrometry showed poor immunogenicity and CD8 T cells specific for MAGE-D1 were not detectable in the tumor bed (data not shown).

Figure 4C:
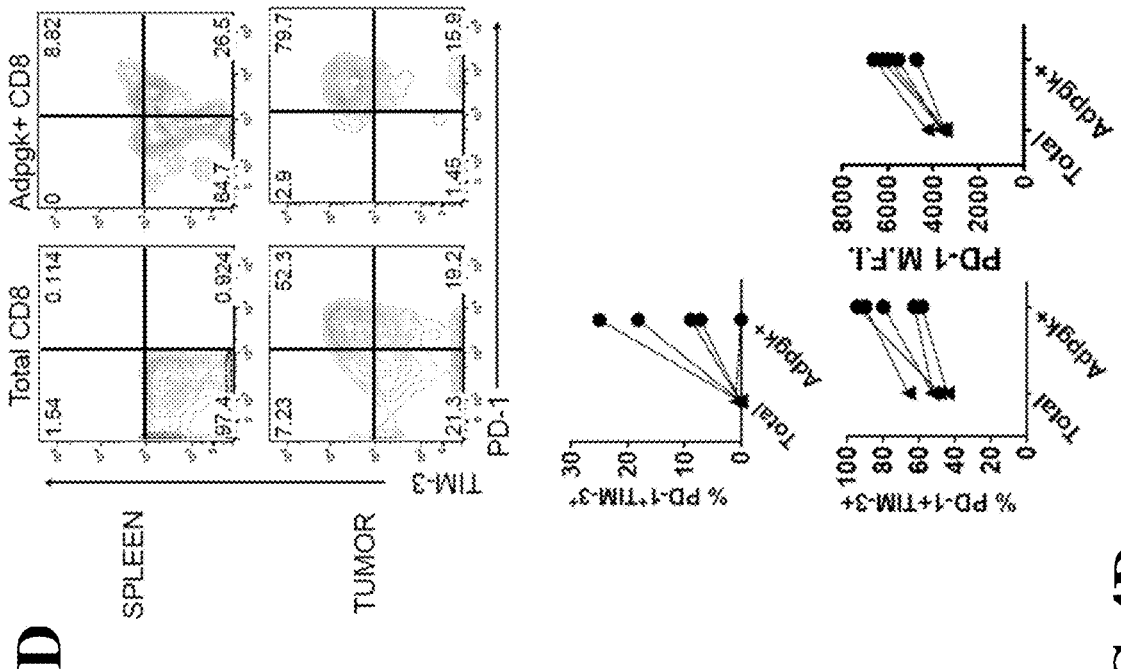
FIG. 4C shows measure of CD8 T cells and CD45 T cells in relation to tumor volume.
Figure 4D:
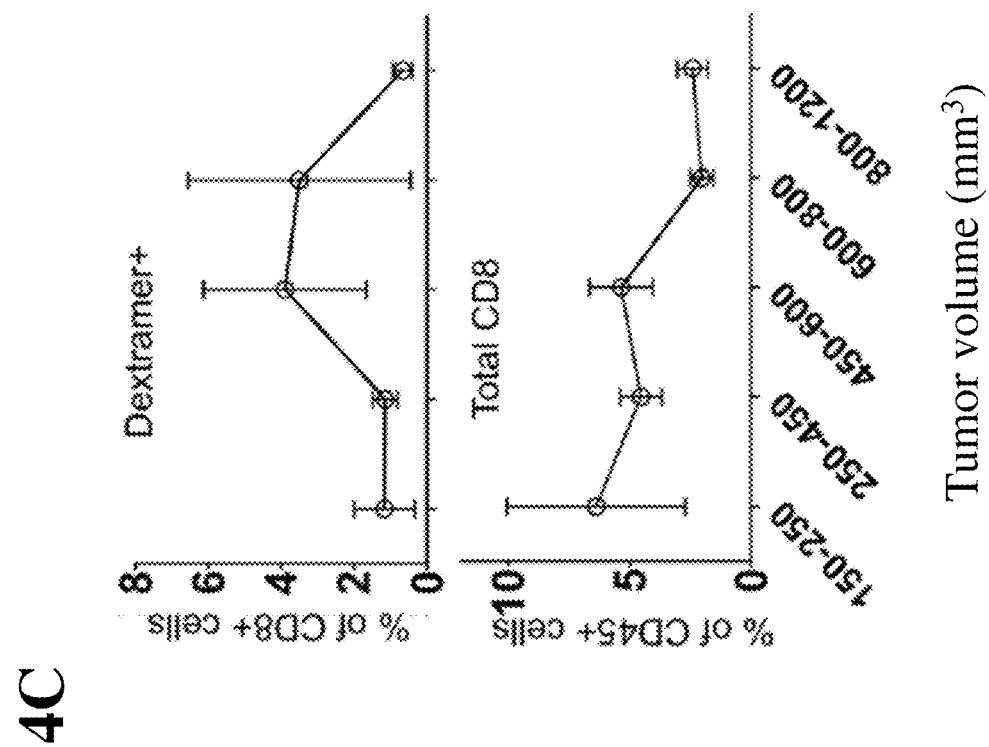
FIG. 4D illustrates percentage of tumor-specific CD8 TILs co-expressing PD-1 and TIM-3 in the total CD8 TIL population and Adpgk positive CD8 TIL population.

Bulk TILs are usually analyzed to monitor anti-tumor responses, which may not provide a true assessment because only a fraction of the TILs are tumor-specific. The frequency and the phenotype of the anti-tumor TILs in comparison to the bulk TILs was examined using MHCI/peptide-specific dextramers for the three immunogenic peptides. The frequency of tumor-specific CD8 T cells infiltrating tumors increased at first, and declined as the tumors grew further, suggesting an inverse correlation of tumor growth with the frequency of tumor-specific CD8 T cells in the tumor (FIG. 4C). Interestingly, a majority (76.9±7.1%) of tumor-specific CD8 TILs co-expressed PD-1 and TIM-3, the markers of T cell exhaustion compared to bulk TILs (52.6±3.6%) (FIG. 4D). Tumor-specific CD8 TILs also expressed higher level of surface PD-1.

Figure 5A:
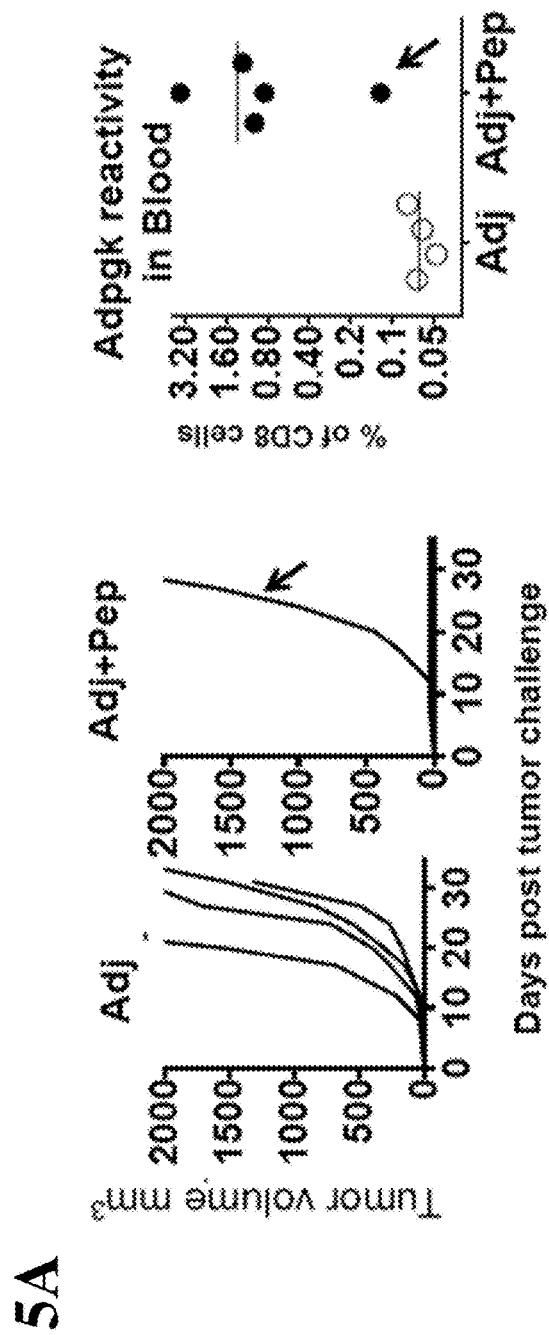
FIG. 5A illustrates tumor volume of mice treated with a control and an immunogenic vaccine following tumor challenge with MC-38 tumor cells, and the percentage of Adpgk positive CD8 T cells following vaccination. The arrow indicates measurements from a single animal.

To determine if CD8 T cells induced against neoepitopes could provide protective anti-tumor immunity, healthy mice were immunized with the mutated peptide vaccine and subsequently challenged with MC-38 tumor cells. Tumor growth was completely inhibited in most of the animals in the vaccine group as compared to adjuvant alone (FIG. 5A). The single animal that grew a tumor in this experiment actually did not respond to the vaccine strongly supporting the possibility that CD8 T cell responses specific to mutated peptides conferred protection (FIG. 5A).

Figure 5B:
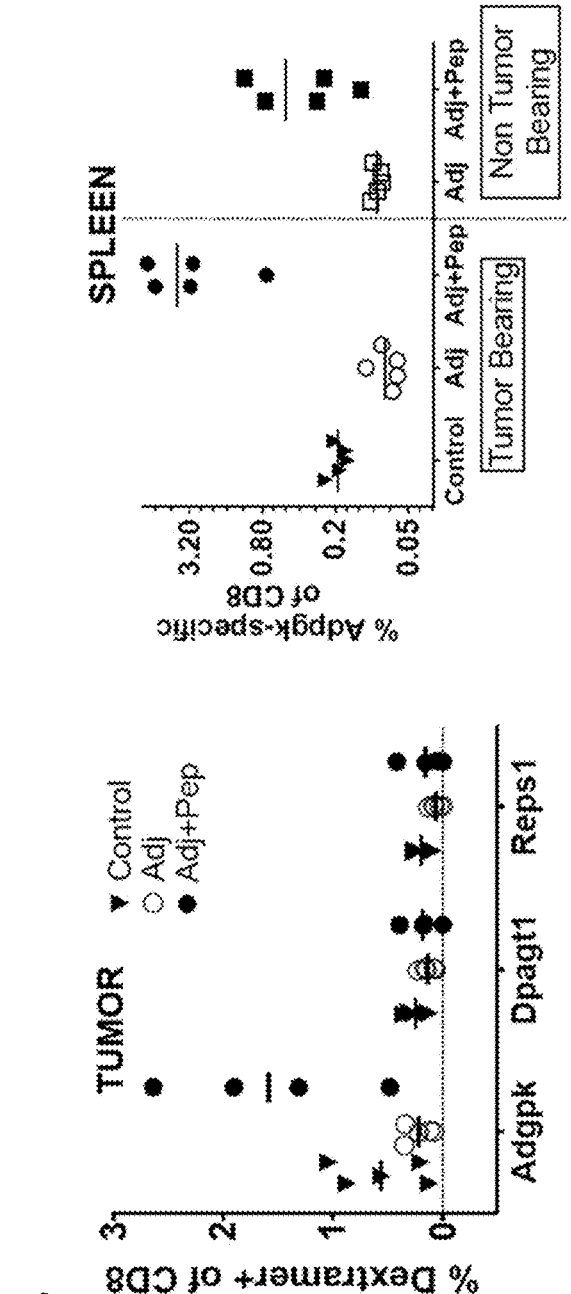
FIG. 5B illustrates percentage of peptide-specific CD8 T cells in the spleen and tumor.
Figure 5C:
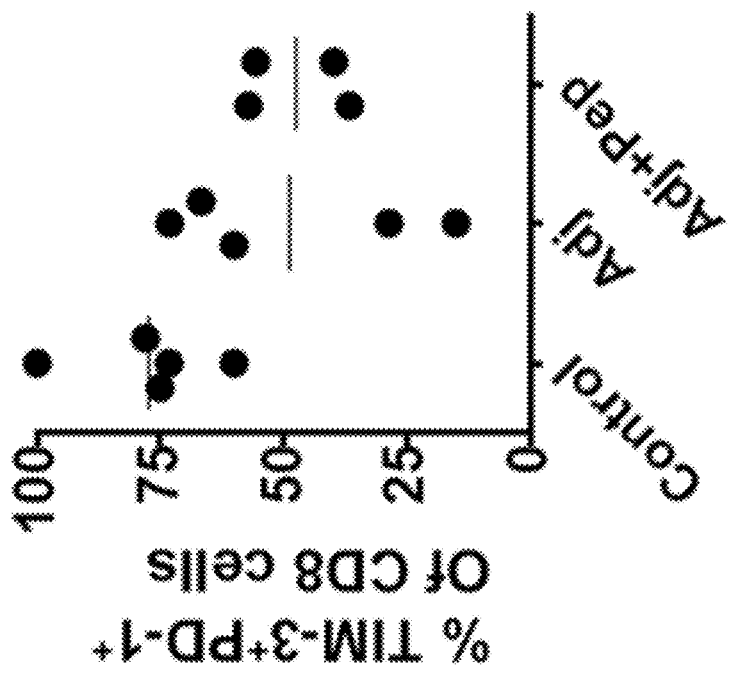
FIG. 5C illustrates percentage of live cells in the tumor measured as CD45 expressing T cells and CD8 expressing T cells.

Next, the neoepitope-specific CD8 T cell responses were evaluated to see if they could be further amplified in tumor-bearing mice upon immunization. After a single immunization, the frequency of Adpgk-reactive CD8 T cells increased remarkably in the spleen of tumor-bearing mice compared to naïve healthy animals (FIG. 4B). It was also observed nearly three-fold increase in accumulation of Adgpk-specific CD8 T cells among total CD8 TILs in the tumors (FIG. 5B). Peptide vaccination also increased overall infiltration of CD45$^+$ cells and CD8$^+$ T cells in tumors, which resulted into nearly 20-fold increase in the frequency of neoepitope-specific CD8 T cells among the total live cells in the tumor (FIG. 5C).

Figure 5D:
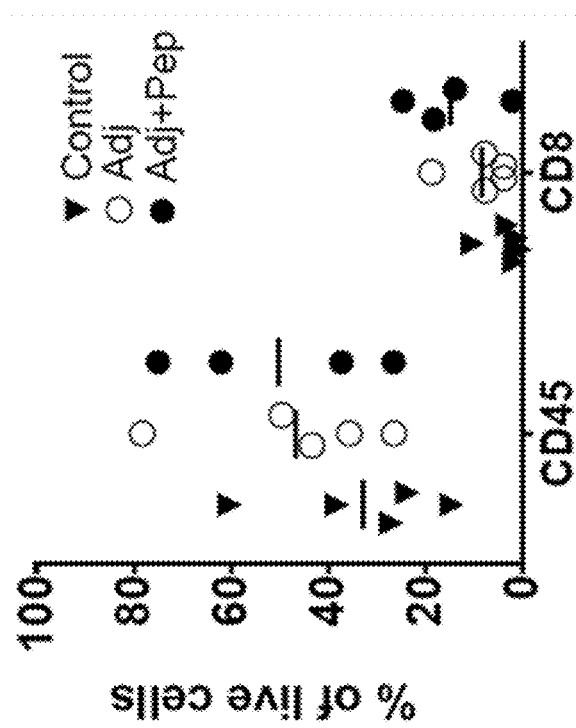
FIG. 5D illustrates percentage of Adgpk-specific CD8 TILs co-expressing PD-1 and TIM-3 in the total CD8 T cell population following vaccination.
Figure 5E:
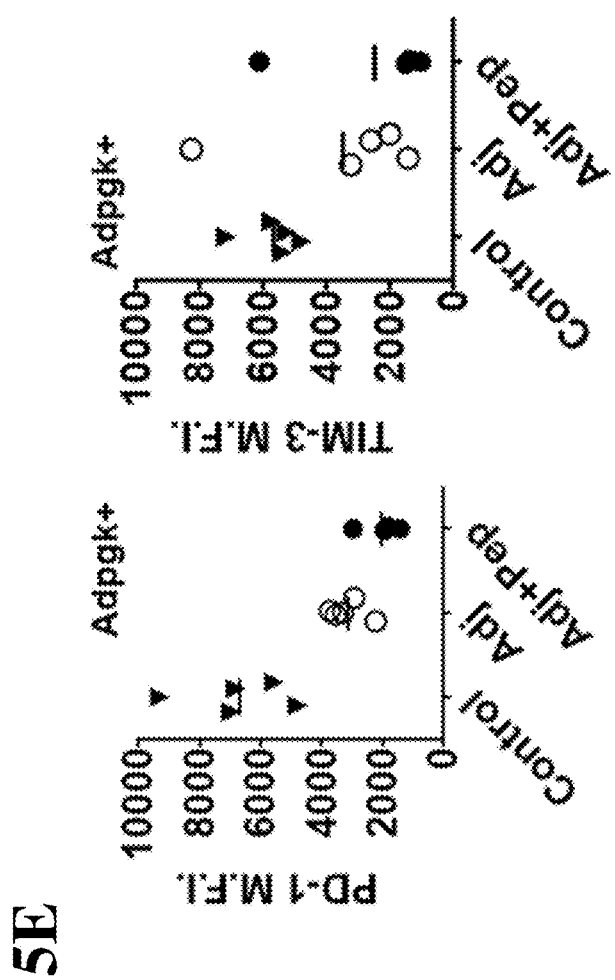
FIG. 5E illustrates level of PD-1 and TIM-3 surface expression following vaccination.
Figure 5F:
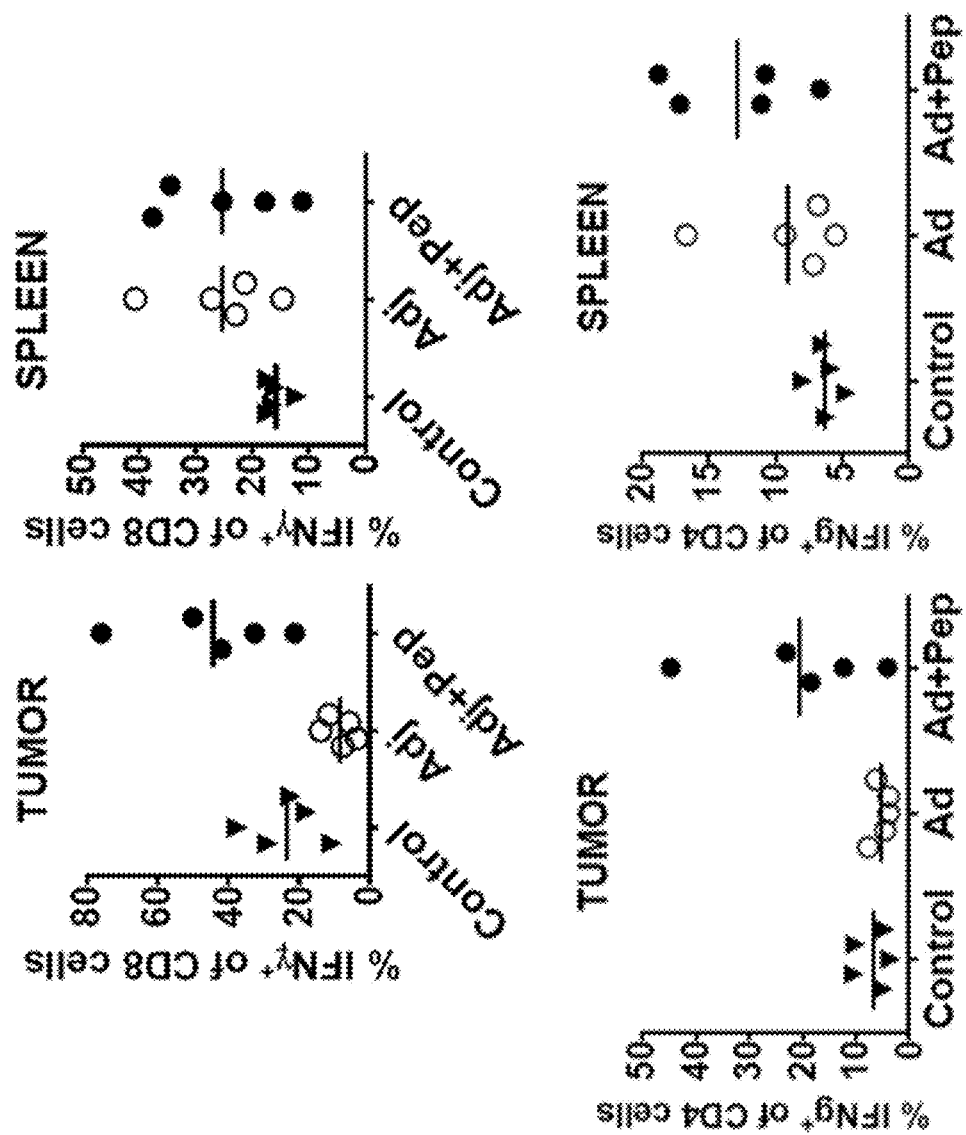
FIG. 5F illustrates percentage of IFN-γ-expressing CD8 and CD4 TILs in tumor and spleen following vaccination.

Furthermore, the phenotype of peptide-specific cells induced by vaccination was analyzed. It was found that the frequency of TIM-3$^+$ PD-1$^+$ Adgpk-specific CD8 TILs was reduced after vaccination, and the surface expression of PD-1 and TIM-3 on these cells was also reduced (FIG. 5D and FIG. 5E). This might be an adjuvant effect as it was also seen in the adjuvant alone group. This result suggests that tumor-specific T cells exhibit a less exhausted phenotype after vaccination, and this was further confirmed by the higher percentage of IFN-γ-expressing CD8 and CD4 TILs in the vaccinated tumors (FIG. 5F).

Figure 5G:
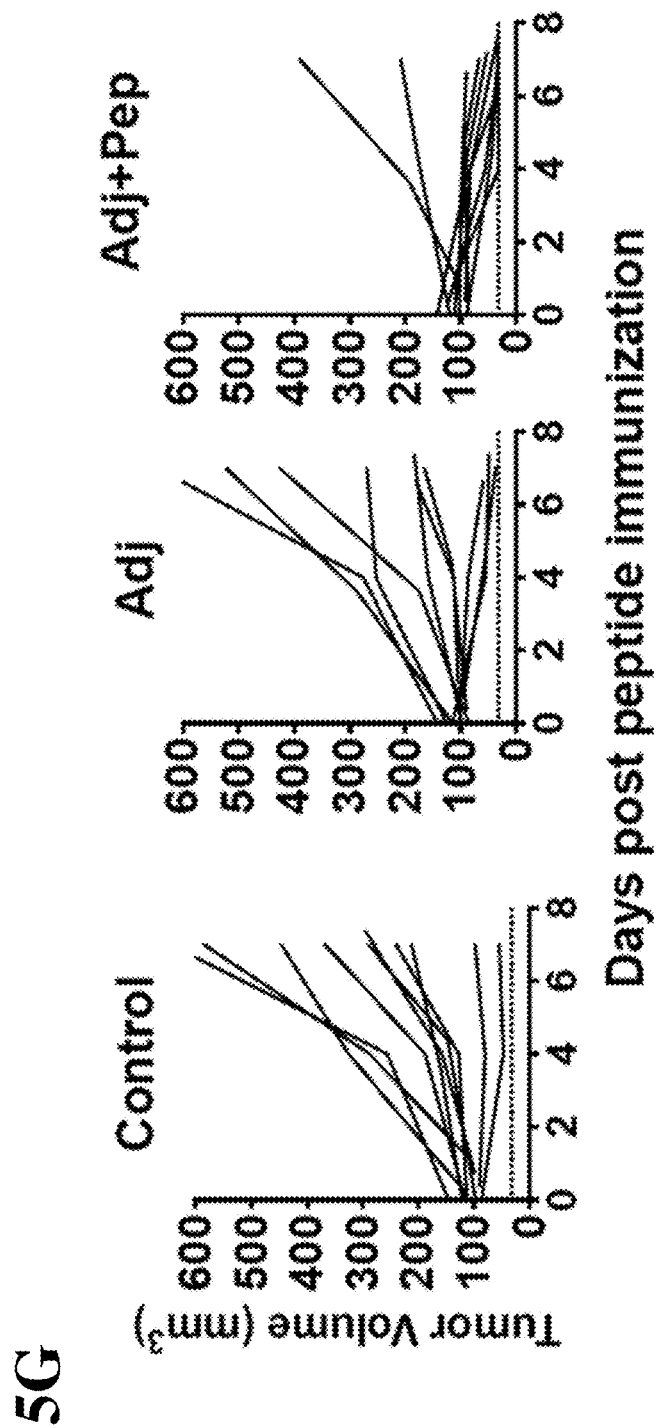
FIG. 5G illustrates measurement of tumor volume following vaccination.

Finally, it was evaluated if these vaccine-induced qualitative and quantitative changes in tumor-specific CD8 T cells could translate into regression of established tumors. Even in this more difficult therapeutic setting vaccinated mice showed remarkable inhibition of tumor growth compared to untreated control or adjuvant alone groups (FIG. 5G). Thus, simple peptide vaccination with the predicted neoepitopes generated sufficient T cell immunity to reject a previously established tumor.

Methods

MHCI peptide profiling was conducted for the H-2Kb and H-2Db ligandome of two murine cell lines of H-2b-background: TRAMP-C1 (ATCC) and MC-38 (Academisch Ziekenhuis Leiden). Cells derived from C57BL/6 mice were prepared as previously described. Reference is made to U.S. patent application Ser. No. 13/087,948 and U.S. patent application Ser. No. 11/00,474 for complete description of methods of preparing cell lines. MHCI molecules of each sample were immunoprecipitated using two different antibodies to extract H-2Kb specific and H-2Db specific peptides, respectively. Peptides were separated by reversed-phase chromatography (nanoAcquity UPLC system, Waters, Milford, Mass.) using a 180-minute gradient. The eluted peptides were analyzed by data-dependent acquisition (DDA) in an LTQ-Orbitrap Velos hybrid mass spectrometer (Thermo Fisher Scientific, Bremen, Germany) equipped with an electrospray ionization (ESI) source. Mass spectral data was acquired using methods comprised of a full scan (survey scan) of high mass accuracy in the Orbitrap (R=30,000 for TOP3, R=60,000 for TOPS), followed by MS/MS (profile) scans either in the Orbitrap (R=7500) on the 5 most abundant precursor ions (TOPS) or in the LTQ on the 3 most abundant precursor ions (TOP3). Seven replicate injections and analyses were performed for each set of samples.

Synthetic peptides corresponding to identify mutant MC-38 and TRAMP-C1 antigen peptides were analyzed on an LTQ-Orbitrap Elite mass spectrometer (ThermoFisher, Bremen, Germany) and ionized using an ADVANCE source (Michrom-Bruker, Fremont, Calif.) at a spray voltage of 1.2 kV. Mass spectral data were acquired using a method consisting of one full MS scan (375-1600 m/z) in the Orbitrap at resolution of 60,000 M/ΔM at m/z 400, followed by MS/MS (centroid) scans in the LTQ of the peptide fragment ions.

1 μg of total RNA from MC-38 and TRAMP-C1 cancer cell lines was used to generate RNA-Seq libraries using TruSeq RNA sample preparation kit (Illumina, CA). Total RNA was purified from cell lines and fragmented to 200-300 base pairs (bp), with an average length of 260 bp. RNA-Seq libraries were multiplexed (two per lane) and sequenced on HiSeq 2000 as per manufacturer's recommendation (Illumina, CA).

Greater than about 50 million paired-end (2×100 bp) sequencing reads were generated per sample. Exome capture was performed using SureSelect Human All Exome kit (50 Mb) (Agilent, CA). Exome capture libraries were then sequenced on a HiSeq 2000 (Illumina, CA) using the HiSeq sequencing Kit (200 cycles).

92.9 million (M) RNA fragments were sequenced from MC-38 and 65.3 M from TRAMP-C1. For exome sequencing, 60M reads were sequenced from each cell line. Reads were mapped to the mouse genome (NCBI build 37 or mm9) using GSNAP (Wu and Nacu, *Bioinformatics*, 2010, v. 26, 873-881). Only uniquely mapped reads were retained for further analysis. 80.6 M RNA fragments were uniquely mapped in the MC-38 sample and 57.6 M in the TRAMP-C1 sample. 50.9 M exome fragments in MC-38 and 52 M fragments in TRAMP-C1 were uniquely mapped. To obtain mouse gene models, Refseq mouse genes were mapped to the mm9 genome using GMAP, and the genomic sequence was then used for making the gene models.

Exome-seq based variants were called using GATK1. Variants with 10% or greater allelic frequency were retained. Variants were annotated for effects on transcripts using the variant effect predictor tool 2. Only the variants for which an amino acid change can be interpreted were retained. In order to obtain variants with evidence of expression, the exome-based variant positions were checked for evidence of variation with RNA-Seq read alignments. Variants that were corroborated by more than 2 RNA-Seq reads and expressed at 10% or more allelic frequency based on RNA-Seq were retained.

For each amino acid variation, a variant whole protein sequence was generated to form a set of putative proteins to serve as a reference database for searching LC-MS spectra. In the absence of haplotype information, multiple variations in the same protein would feature as separate variant proteins in the database.

Tandem mass spectral results were submitted for protein database searching using the Mascot algorithm version 2.3.02 (MatrixScience, London, UK) against a concatenated target decoy database Uniprot version 2011_12 or a transcriptome generated FASTA database; comprising of murine proteins and common laboratory contaminants such as trypsin. The data was searched with no enzyme specificity, methionine oxidation (+15.995 Da), and 20 ppm precursor ion mass tolerance.

Fragment ion mass tolerance was specified at 0.8 Da or 0.05 Da for MS/MS data acquired in the LTQ or Orbitrap, respectively. Search results were filtered using a linear discriminant algorithm (LDA) to an estimated peptide false discovery rate (FDR) of 5%. For higher confidence in mutant peptide identifications, the data was further filtered either by peptide length, 8 for H-2Kb data and 9 for H-2Db or employing regular expressions to isolate peptides with the following well characterized anchor motifs H-2Kb: XXXX[FY]XX[MILV] (SEQ ID NO. 22) and H-2Db: XXXX[N]XXX[MIL] (SEQ ID NO. 23). Synthetic peptides were generated to validate the sequences.

For generation of first models, peptide-MHC complex structures were chosen from the PDB based on sequence similarity between the mutant peptide and peptide in the model structure. For each mutant peptide model, the following PDB code was used: Reps1, 2ZOL 4; Adpgk, 1HOC 5; Dpagt1, 3P9L 6; Cpne1, 1JUF7; Irgq, 1FFN 8; Aatf, 1BZ9. The Med12 peptide was not modeled due to a lack of a published H-2Kb crystal structure in complex with 10-mer peptide that could be used as a reasonable starting model. The peptide was then modified to the mutant form using COOT 10. These first models were then optimized using the Rosetta FlexPepDock web server 11, and the top scoring model chosen for display.

The top scoring FlexPepDock models for each peptide were also inspected, and backbone positioning was found to be similar for the top ten models generated. Peptide-MHC images were generated using Pymol (Schrödinger, LLC).

Age-matched 6-8 weeks old C57BL/6 mice (The Jackson Laboratory) were injected intraperitonealy with 50 mg long peptide each in combination with adjuvant (50 μg anti-CD40 Ab clone FJK45 plus 100 mg poly(I:C) (Invivogen)) in PBS. Mice were immunized on day 0 and day 14 and one week following the last injection, either blood or splenocytes were used for detection of Ag-specific CD8 T cells. To identify peptide-specific T cells, cells were stained with PE-conjugated dextramers (MHCI/peptide complex; Immudex, Denmark) for 20 min followed by staining with cell surface markers CD3, CD4, CD8 and B220 (BD Biosciences). Peptide sequences were as follows Reps1: GRVLELFRAAQLANDVVLQIMELCGATR (SEQ ID NO. 1); Adpgk: GIPVHLELASMTNMELMSSIVHQQVFPT (SEQ ID NO. 2); Dpagt1: EAGQSLVISASIIVFNLLELEGDYR (SEQ ID NO. 3); Aatf: SKLLSFMAPIDHTTMSDDARTELFRS (SEQ ID NO. 4); Irgq: KARDETAALLNSAVLGAAPLFVPPAD (SEQ ID NO. 5); Cpne1: DFTGSNGDPSSPYSLHYLSPTGVNEY (SEQ ID NO. 6); Med12: GPQEKQQRVELSSISNFQAVSELLTFE (SEQ ID NO. 7).

C57BL/6 mice were implanted subcutaneously on the right flank with 1×10⁵ MC-38 tumor cells. The whole tumor was isolated and digested with collagenase and DNAase to isolate TILs. TILs were stained with dextramers (as described above) followed by antibodies against CD45, Thy1.2, CD4, CD8 (BD Biosciences), PD-1 (eBiosciences) and TIM-3 (R&D Systems). Live/dead stain was used to gate on live cells.

All animals were inoculated subcutaneously (right hind flank) with 1×10⁵ MC-38 cells in a suspension of Hanks' balanced salt solution (HBSS) and phenol red-free matrigel (Becton Dickinson Bioscience, San Jose, Calif.). For prophylactic studies mice were immunized with adjuvant (50 mg anti-CD40 plus 100 mg poly(I:C) or adjuvant with 50 μg Reps1, Adpgk and Dpagt1 peptide each 3 weeks before the tumor inoculation. Induction of peptide-specific CD8 T cells was measured in blood a day prior to inoculation with tumor cells. For vaccination in tumor bearing mice, 10 days after inoculation with 1×105 MC-38 tumor cells (only tumor with volume of approximately 100-150 mm³ at day 10 were included in the study) mice were injected with adjuvant or adjuvant with 50 μg Reps1, Adpgk, and Dpagt1 peptide each. Measurements and weights were collected twice a week. Animals exhibiting weight loss of more than 15% of their first body weight were weighed daily and euthanized if they lose more than 20% of their first body weight.

Animals that exhibited adverse clinical issues were observed more frequently, up to daily depending on the severity, and euthanized if moribund. Mice were euthanized if tumor volumes exceeded 3,000 mm³, or after 3 months if tumors did not form. Throughout the entire study, clinical observations of all mice were performed twice a week.

TABLE 1

Summary of mutant peptides presented on MHCI in the MC-38 cell line.

| Gene | Peptide* | MHC Allele | IC50 (mutant) (nM) | IC50 (WT) (nM) | Mutation Position | Immunogenicity Prediction |
|---|---|---|---|---|---|---|
| Dpagt1 | SIIVFNLV (SEQ ID NO. 8) SIIVFNLL (SEQ ID NO. 9) | H-2Kb | 8 | 34 | Anchor (P8) | − |
| Reps1 | AQLPNDVVL (SEQ ID NO. 10) AQLANDVVL (SEQ ID NO. 11) | H-2Db | 9 | 100 | Solvent (P4) | + |
| Adpgk | ASMTNRELM (SEQ ID NO. 12) ASMTNMELM (SEQ ID NO. 13) | H-2Db | 2 | 3 | Solvent (P6) | + |
| Cpne1 | SSPDSLHYL (SEQ ID NO. 14) SSPYSLHYL (SEQ ID NO. 15) | H-2Db | 211 | 685 | Solvent (P4) | − |
| Irgq | AALLNSAGL (SEQ ID NO. 16) AALLNSAVL (SEQ ID NO. 17) | H-2Db | 3 | 52 | Solvent (P8) | − |
| Aatf | MAPIDHTAM (SEQ ID NO. 18) MAPIDHTTM (SEQ ID NO. 19) | H-2Db | 30 | 102 | Solvent (P8) | − |
| Med12 | DPSSSVLFED (SEQ ID NO. 20) DPSSSVLFEY (SEQ ID NO. 21) | H-2Kb | 38300 | 39411 | No structure | − |

*The top-listed sequence for each gene is the WT sequence and the bottom-listed sequence for each gene is the mutant sequence.

What is claim is:

1. A method of identifying a disease-specific immunogenic mutant peptide from a disease tissue in an individual, comprising:
   (a) obtaining a first set of variant-coding sequences based on the genomic sequences of the disease tissue in the individual, each variant-coding sequence of the first set having a sequence variation compared to a reference sample;
   (b) selecting a second set of expression variant-coding sequences from the first set based on transcriptomic sequences of the disease tissue in the individual;
   (c) selecting a third set of epitope variant-coding sequences from the second set based on predicted ability of the peptides encoded by the second set to bind to an MHC class I molecule (MHCI);
   (d) obtaining a plurality of peptides that are bound to an MHCI from the disease tissue;
   (e) subjecting the MHCI-bound peptides to mass spectrometry-based sequencing,
      wherein mass spectrometry-based sequencing comprises identifying MHCI-bound peptides based on transcriptomic sequence information of the disease tissue; and
   (f) correlating the mass spectrometry-derived sequence information of the MHCI-bound peptides with the third set of epitope variant-coding sequences, thereby identifying the disease-specific immunogenic mutant peptide.

2. The method of claim 1, wherein the obtaining the first set of variant-coding sequences based on genomic sequences of the disease tissue in the individual comprises:
   (i) obtaining a set of sequences based on the genomic sequences of the disease tissue in the individual; and
   (ii) identifying the first set of variant-coding sequences from the set of sequences,
      wherein each variant-coding sequence of the first set of variant-coding sequences comprises a variation in the sequence compared to the reference sample.

3. The method of claim 1, further comprising synthesizing a nucleic acid encoding a peptide based on the sequence of the identified disease-specific immunogenic mutant peptide.

4. The method of claim 1, wherein the disease is cancer.

5. The method of claim 1, wherein the individual is human.

6. A method of stimulating an immune response in the individual of claim 1 with the disease of claim 1 comprising:
   (a) identifying according to claim 1 the disease-specific immunogenic mutant peptide from the disease tissue in the individual;
   (b) producing a composition comprising a peptide or a nucleic acid encoding the peptide based on the sequence of the identified disease-specific immunogenic mutant peptide; and
   (c) administering the composition to the individual.

7. The method of claim 6, further comprising administering an anti-PD-1 antibody to the individual.

8. The method of claim 6, further comprising administering to the individual an anti-PD-L1 antibody to the individual.

9. The method of claim 1, further comprising predicting immunogenicity of peptides identified in step (f).

10. The method of claim 9, wherein predicting immunogenicity is based on one or more of the following parameters:
   (i) binding affinity of the peptide to the MHCI molecule;
   (ii) protein level of a peptide precursor containing the peptide;
   (iii) expression level of the transcript encoding the peptide precursor;
   (iv) processing efficiency of the peptide precursor by an immunoproteasome;
   (v) timing of expression of the peptide precursor;
   (vi) binding affinity of the peptide to a TCR molecule;
   (vii) position of a variant amino acid within the peptide;
   (viii) solvent exposure of the peptide when bound to a MHCI molecule;

(ix) solvent exposure of the variant amino acid when bound to a MHCI molecule;
(x) content of aromatic residues in the peptide;
(xi) property of the variant amino acid when compared to the wild type residue; and
(xii) nature of the peptide precursor.

11. The method of claim 10, wherein the prediction of immunogenicity further comprises HLA-typing analysis.

* * * * *

SEQUENCE LISTING

<160> NUMBER OF SEQ ID NOS: 23

<210> SEQ ID NO 1
<211> LENGTH: 28
<212> TYPE: PRT
<213> ORGANISM: Artificial Sequence
<220> FEATURE:
<223> OTHER INFORMATION: Synthetic Construct

<400> SEQUENCE: 1

Gly Arg Val Leu Glu Leu Phe Arg Ala Ala Gln Leu Ala Asn Asp Val
1               5                   10                  15

Val Leu Gln Ile Met Glu Leu Cys Gly Ala Thr Arg
            20                  25

<210> SEQ ID NO 2
<211> LENGTH: 28
<212> TYPE: PRT
<213> ORGANISM: Artificial Sequence
<220> FEATURE:
<223> OTHER INFORMATION: Synthetic Construct

<400> SEQUENCE: 2

Gly Ile Pro Val His Leu Glu Leu Ala Ser Met Thr Asn Met Glu Leu
1               5                   10                  15

Met Ser Ser Ile Val His Gln Gln Val Phe Pro Thr
            20                  25

<210> SEQ ID NO 3
<211> LENGTH: 25
<212> TYPE: PRT
<213> ORGANISM: Artificial Sequence
<220> FEATURE:
<223> OTHER INFORMATION: Synthetic Construct

<400> SEQUENCE: 3

Glu Ala Gly Gln Ser Leu Val Ile Ser Ala Ser Ile Ile Val Phe Asn
1               5                   10                  15

Leu Leu Glu Leu Glu Gly Asp Tyr Arg
            20                  25

<210> SEQ ID NO 4
<211> LENGTH: 26
<212> TYPE: PRT
<213> ORGANISM: Artificial Sequence
<220> FEATURE:
<223> OTHER INFORMATION: Synthetic Construct

<400> SEQUENCE: 4

Ser Lys Leu Leu Ser Phe Met Ala Pro Ile Asp His Thr Thr Met Ser
1               5                   10                  15

Asp Asp Ala Arg Thr Glu Leu Phe Arg Ser
            20                  25

<210> SEQ ID NO 5
<211> LENGTH: 26
<212> TYPE: PRT
<213> ORGANISM: Artificial Sequence
<220> FEATURE:
<223> OTHER INFORMATION: Synthetic Construct

<400> SEQUENCE: 5

Lys Ala Arg Asp Glu Thr Ala Ala Leu Leu Asn Ser Ala Val Leu Gly
1               5                   10                  15

Ala Ala Pro Leu Phe Val Pro Pro Ala Asp
            20                  25

<210> SEQ ID NO 6
<211> LENGTH: 26
<212> TYPE: PRT
<213> ORGANISM: Artificial Sequence
<220> FEATURE:
<223> OTHER INFORMATION: Synthetic Construct

<400> SEQUENCE: 6

Asp Phe Thr Gly Ser Asn Gly Asp Pro Ser Ser Pro Tyr Ser Leu His
1               5                   10                  15

Tyr Leu Ser Pro Thr Gly Val Asn Glu Tyr
            20                  25

<210> SEQ ID NO 7
<211> LENGTH: 27
<212> TYPE: PRT
<213> ORGANISM: Artificial Sequence
<220> FEATURE:
<223> OTHER INFORMATION: Synthetic Construct

<400> SEQUENCE: 7

Gly Pro Gln Glu Lys Gln Gln Arg Val Glu Leu Ser Ser Ile Ser Asn
1               5                   10                  15

Phe Gln Ala Val Ser Glu Leu Leu Thr Phe Glu
            20                  25

<210> SEQ ID NO 8
<211> LENGTH: 8
<212> TYPE: PRT
<213> ORGANISM: Artificial Sequence
<220> FEATURE:
<223> OTHER INFORMATION: Synthetic Construct

<400> SEQUENCE: 8

Ser Ile Ile Val Phe Asn Leu Val
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic Construct

<400> SEQUENCE: 9

Ser Ile Ile Val Phe Asn Leu Leu
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Construct

<400> SEQUENCE: 10

Ala Gln Leu Pro Asn Asp Val Val Leu
1               5

<210> SEQ ID NO 11
<211> LENGTH: 9
<212> TYPE: PRT
<213> ORGANISM: Artificial Sequence

```
<220> FEATURE:
<223> OTHER INFORMATION: Synthetic Construct

<400> SEQUENCE: 11

Ala Gln Leu Ala Asn Asp Val Val Leu
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic Construct

<400> SEQUENCE: 12

Ala Ser Met Thr Asn Arg Glu Leu Met
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic Construct

<400> SEQUENCE: 13

Ala Ser Met Thr Asn Met Glu Leu Met
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Construct

<400> SEQUENCE: 14

Ser Ser Pro Asp Ser Leu His Tyr Leu
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic Construct

<400> SEQUENCE: 15

Ser Ser Pro Tyr Ser Leu His Tyr Leu
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Construct

<400> SEQUENCE: 16

Ala Ala Leu Leu Asn Ser Ala Gly Leu
1               5

<210> SEQ ID NO 17
<211> LENGTH: 9
<212> TYPE: PRT
<213> ORGANISM: Artificial Sequence
<220> FEATURE:
```

```
<223> OTHER INFORMATION: Synthetic Construct

<400> SEQUENCE: 17

Ala Ala Leu Leu Asn Ser Ala Val Leu
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Construct

<400> SEQUENCE: 18

Met Ala Pro Ile Asp His Thr Ala Met
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic Construct

<400> SEQUENCE: 19

Met Ala Pro Ile Asp His Thr Thr Met
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic Construct

<400> SEQUENCE: 20

Asp Pro Ser Ser Ser Val Leu Phe Glu Asp
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic Construct

<400> SEQUENCE: 21

Asp Pro Ser Ser Ser Val Leu Phe Glu Tyr
1               5                   10

<210> SEQ ID NO 22
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 6, 7
<223> OTHER INFORMATION: Xaa = Any Amino Acid
<220> FEATURE:
<221> NAME/KEY: VARIANT
<222> LOCATION: 5
<223> OTHER INFORMATION: Xaa = Phe or Tyr
<220> FEATURE:
<221> NAME/KEY: VARIANT
<222> LOCATION: 8
<223> OTHER INFORMATION: Xaa = Met, Ile, Leu or Val
```

```
<400> SEQUENCE: 22

Xaa Xaa Xaa Xaa Xaa Xaa Xaa Xaa
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 6, 7, 8
<223> OTHER INFORMATION: Xaa = Asp or Gly
<220> FEATURE:
<221> NAME/KEY: VARIANT
<222> LOCATION: 5
<223> OTHER INFORMATION: Xaa = Asn
<220> FEATURE:
<221> NAME/KEY: VARIANT
<222> LOCATION: 9
<223> OTHER INFORMATION: Xaa = Met, Ile or Leu

<400> SEQUENCE: 23

Xaa Xaa Xaa Xaa Xaa Xaa Xaa Xaa Xaa
1               5
```